United States Patent
Caldwell et al.

(10) Patent No.: US 6,372,733 B1
(45) Date of Patent: *Apr. 16, 2002

(54) HEXAHYDRO-5-IMINO-1,4-1,4-THIAZEPINE DERIVATIVES AS INHIBITORS OF NITRIC OXIDE SYNTHASES

(75) Inventors: Charles G. Caldwell, Scotch Plains; Malcolm Maccoss, Freehold; William K. Hagmann, Westfield; Shrenik K. Shah, Metuchen; Kothandaraman Shankaran, Kendall Park; Karla L. Furman, Red Bank, all of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/477,246

(22) Filed: Jan. 4, 2000

Related U.S. Application Data

(62) Division of application No. 08/721,784, filed on Sep. 25, 1996, now Pat. No. 6,043,358.
(60) Provisional application No. 60/007,172, filed on Nov. 1, 1995, and provisional application No. 60/009,012, filed on Dec. 21, 1995.

(51) Int. Cl.$^7$ .................. C07D 28/06; C07D 28/08; A61K 31/554; A61P 15/10

(52) U.S. Cl. .................. 514/211.01; 514/211.09; 540/466; 540/467; 540/468

(58) Field of Search .................. 514/211.01, 211.09; 540/466, 467, 468

(56) References Cited

U.S. PATENT DOCUMENTS

| | | | | |
|---|---|---|---|---|
| 3,351,632 A | * | 11/1967 | Griot | 260/327 |
| 4,096,140 A | | 6/1978 | Simpson | 260/239 |
| 5,629,322 A | | 5/1997 | Guthikonda et al. | 514/313 |
| 5,854,234 A | | 12/1998 | Hansen, Jr. et al. | 514/212 |

FOREIGN PATENT DOCUMENTS

| | | | |
|---|---|---|---|
| CH | 422793 | * | 4/1967 |
| EP | 0 129 692 | | 1/1985 |
| FR | 1 508 536 | | 3/1968 |
| FR | 2 292 479 | | 6/1976 |
| IN | 145296 | * | 9/1978 |
| WO | WO 95/11231 | | 4/1995 |
| WO | WO 96/14844 | | 5/1996 |
| WO | WO 96/35677 | | 11/1996 |

OTHER PUBLICATIONS

"Steadman's Medical Dictionary", Williams & Wikins, Montvale, NJ.*
Bennett, J.C. and Plum, F. eds.,"Cecil Textbook of Medicine 20th Ed." 1996, W.B. Saunders Company, Philadelphia.*
Berkow, R. Ed.–in–Chief, "The Merck Manual of Diagnosis and Therapy, 16th Ed.", 1992, Merck & co., Rahway, NJ, p2801.*
Schmutz, Jean; Kuenzle, G.; Hunziker, Fritz; Gauch, R., Helv. Chim. Acta, 50(1), 245–54 (German) 1967.*
Walia, Jasjit S.; Walia, Amrik S.; Lankin, David C.; Petterson, Robert C.; Singh, Janak, J. Heterocycl. Chem., 22(4), 1117–19 (English) 1985.*
Caujolle, R.; Baziard–Mouysset, G.; Favrot, J. D.; Payard, M.; Loiseau, P. R.; Amarouch, H.; Linas, M. D.; Seguela, J. P.; Loiseau, P. M.; et al., Eur. J. Med. Chem., 28(1), 29–35 (French) 1993.*
Ambrogi, V.; Grandolini, G.; Perioli, L.; Giusti, L.; Lucacchini, A.; Martini, C., Eur. J. Med. Chem., 30(5), 429–37 (Enghlish) 1995.*
Erker, Thomas; Bartsch, Herbert, Monatsh. Chem., 123(11), 1023–6 (German) 1992.*
Bartsch, Herbert; Erker, Thomas J. Heterocycl. Chem., 25(5), 1399–401 (English) 1988.*
Wuensch, Karl H.; Ehlers, Annerose, Chem. Ber., 102(6), 1869–75 (German) 1969.*
Arya, V. P., Chem. Abs., vol. 92, No. 17, Abs. No. 146818, 1980.

(List continued on next page.)

*Primary Examiner*—Mukund J. Shah
*Assistant Examiner*—Thomas McKenzie
(74) *Attorney, Agent, or Firm*—Raynard Yuro; Curtis C. Panzer; David L. Rose

(57) ABSTRACT

Disclosed herein are compounds of Formula I

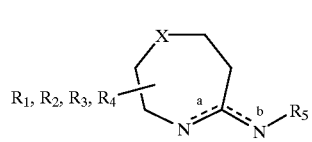

and pharmaceutically acceptable salts thereof which have been found useful in the treatment of nitric oxide synthase mediated diseases and disorders, including neurodegenerative disorders, disorders of gastrointestinal motility and inflammation. These diseases and disorders include hypotension, septic shock, toxic shock syndrome, hemodialysis, IL-2 therapy such as in in cancer patients, cachexia, immunosuppression such as in transplant therapy, autoimmune and/or inflammatory indications including sunburn, eczema or psoriasis and respiratory conditions such as bronchitis, asthma, oxidant-induced lung injury and acute respiratory distress (ARDS), glomerulonephritis, restenosis, inflammatory sequelae of viral infections, myocarditis, heart failure, atherosclerosis, osteoarthritis, rheumatoid arthritis, septic arthritis, chronic or inflammatory bowel disease, ulcerative colitis, Crohn's disease, systemic lupus erythematosis (SLE), ocular conditions such as ocular hypertension, retinitis and uveitis, type 1 diabetes, insulin-dependent diabetes mellitus and cystic fibrosis.

12 Claims, No Drawings

OTHER PUBLICATIONS

Aleshina, G.A., et al.., Chem. Abs., vol. 94, No. 9, Abs. No. 65731, 1981.
Korakas, D., et al., Synthesis, vol. 2, pp. 164–166, 1994.
Hammouda, H.A., et al., Egypt, J. Chem., vol. 30, No. 3, pp. 239–247, 1987.
Takagi, K., et al., Synthesis, vol. 4, pp. 379–381, 1987.
Corral, C. et al., J. of Heterocyclic Chem., vol. 14, No. 6, pp. 985–988, 1977.
Bauer, A., et al., J. Med. Chem., vol. 16, No. 9, pp. 1011–1014, 1973.
Kurihara, T., et al., Chem. Abs., vol. 83, No. 9, Abs. No. 193257, 1975.
Gadzhiev, G. Yu, et al., Zh. Org. Khim., vol. 21, No. 9, pp. 2007–2008, 1985.
Ondrus, T.A., et al., Can. J. Chem., vol. 63, No. 9, pp. 2362–2368, 1985.

* cited by examiner

HEXAHYDRO-5-IMINO-1,4-1,4-THIAZEPINE DERIVATIVES AS INHIBITORS OF NITRIC OXIDE SYNTHASES

This is a division of application Ser. No. 08/721,784, filed Sep. 25, 1996, which is now U.S. Pat. No. 6,043,358, and which claims the benefit of U.S. Provisional Application No. 60/007,172, filed Nov. 1, 1995 and U.S. Provisional Application No. 60/009,012, filed Dec. 21, 1995.

BACKGROUND OF THE INVENTION

This application is directed to inhibitors of nitric oxide synthase, and in particular cyclic amidines.

Nitric Oxide in Biology

The emergence of nitric oxide (NO), a reactive, inorganic radical gas as a molecule contributing to important physiological and pathological processes is one of the major biological revelations of recent times. This molecule is produced under a variety of physiological and pathological conditions by cells mediating vital biological functions. Examples include endothelial cells lining the blood vessels; nitric oxide derived from these cells relaxes smooth muscle and regulates blood pressure and has significant effects on the function of circulating blood cells such as platelets and neutrophils as well as on smooth muscle, both of the blood vessels and also of other organs such as the airways. In the brain and elsewhere nitric oxide serves as a neurotransmitter in non-adrenergic non-cholinergic neurons. In these instances nitric oxide appears to be produced in small amounts on an intermittent basis in response to various endogenous molecular signals. In the immune system nitric oxide can be synthesized in much larger amounts on a protracted basis. Its production is induced by exogenous or endogenous inflammatory stimuli, notably endotoxin and cytokines elaborated by cells of the host defense system in response to infectious and inflammatory stimuli. This induced production results in prolonged nitric oxide release which contributes both to host defense processes such as the killing of bacteria and viruses as well as pathology associated with acute and chronic inflammation in a wide variety of diseases. The discovery that nitric oxide production is mediated by a unique series of three closely related enzymes, named nitric oxide synthases, which utilize the amino acid arginine and molecular oxygen as co-substrates has provided an understanding of the biochemistry of this molecule and provides distinct pharmacological targets for the inhibition of the synthesis of this mediator, which should provide significant beneficial effects in a wide variety of diseases.

Nitric Oxide Synthases

Nitric oxide and L-citrulline are formed from L-arginine via the dioxygenase activity of specific nitric oxide synthases (NOSs) in mammalian cells. In this reaction, L-arginine, $O_2$ and NADPH are cosubstrates while FMN, FAD and tetrahydrobiopterin are cofactors. NOSs fall into two distinct classes, constitutive NOS (cNOS) and inducible NOS (INOS). Two constitutive NOSs have been identified. They are:

(i) a constitutive, $Ca^{++}$/calmodulin dependent enzyme, located in the endothelium and elsewhere (ecNOS or NOS 3), that releases NO in response to receptor or physical stimulation, (ii) a constitutive, $Ca^{++}$/calmodulin dependent enzyme, located in the brain (ncNOS or NOS 1) and elsewhere, that releases NO in response to receptor or physical stimulation, The third isoform identified is inducible NOS (iNOS or NOS 2):

(iii) a $Ca^{++}$ independent enzyme which is induced after activation of vascular smooth muscle, macrophages, endothelial cells, and a large number of other cells by endotoxin and cytokines. Once expressed, this inducible NO synthase produces NO in relatively large amounts for long periods of time.

Spectral studies of both the mouse macrophage INOS and rat brain ncNOS have shown that these enzymes (which have been classified as P-450-like enzymes from their CO-difference spectra) contain a heme moiety. The structural similarity between NOS and the P-450/flavoprotein complex suggests that the NOS reaction mechanism may be similar to P-450 hydroxylation and/or peroxidation. This indicates that NOS belongs to a class of flavohemeproteins which contain both heme and flavin binding regions within a single protein in contrast to the multiprotein NADPH oxidase or Cytochrome P-450/NADPH Cyt c reductase complexes.

Distinct Functions of NO Produced by Different Nitric Oxide Synthases

The NO released by the constitutive enzymes (NOS 1 and NOS 3) acts as an autocoid mediating a number of physiological responses. Two distinct cDNAs accounting for the activity of NOS 1 and NOS 3 in man have been cloned, one for NOS 1 (Nakane et. al., *FEBS Letters*, 316, 175–182, 1993) which is present in the brain and a number of peripheral tissues, the other for an enzyme present in endothelium (NOS 3) (Marsden et. al., *FEBS Letters*, 307, 287–293, 1992). This latter enzyme is critical for production of NO to maintain vasorelaxation. A second class of enzyme, INOS or NOS 2, has been cloned from human liver (Geller et. al., PNAS, 90, 3491–5, 1993), and identified in more than a dozen other cells and tissues, including smooth muscle cells, chondrocytes, the kidney and airways. As with its counterpart from the murine macrophage, this enzyme is induced upon exposure to cytokines such as gamma interferon (IFN-γ), interleukin-1β (IL-1β), tumor necrosis factor (TNF-α) and LPS (lipopolysaccharide). Once induced, iNOS expression continues over a prolonged period of time. The enzyme does not require exogenous calmodulin for activity.

Endothelium derived relaxation factor (EDRF) has been shown to be produced by NOS 3 (Moncada et. al, *Pharmacol Reviews*, 43, 109–142, 1991). Studies with substrate analog inhibitors of NOS have shown a role for NO in regulating blood pressure in animals and blood flow in man, a function attributed to NOS 3. A transgenic mouse deficient in functional NOS 3 was shown to be hypertensive, thus validating the role of NO synthesis by NOS 3 in the regulation of blood pressure (Huang et al., *Nature*, 377, 239–242, 1995). NO has also been shown to be an effector of the cytotoxic effects of activated macrophages (Nathan, *FASEB J.*, 6, 3051–64, 1992) for fighting tumour cells and invading microorganisms (Wright et al., *Card. Res.*, 26,48–57, 1992 and Moncada et al., *Pharmacological Review*, 43, 109–142, 1991). It also appears that the adverse effects of excess NO production, in particular pathological vasodilation and tissue damage, may result largely from the effects of NO synthesized by the NOS 2.

NO generated by NOS 2 has been implicated in the pathogenesis of inflammatory diseases. In experimental animals hypotension induced by LPS or TNF-α can be reversed by NOS inhibitors and reinitiated by L-arginine (Kilboum et.

al., *PNAS*, 87, 3629–32, 1990). Conditions which lead to cytokine-induced hypotension include septic shock, hemodialysis (Beasley and Brenner, *Kidney Int.*, 42, Suppl., 38, S96–S 100, 1992) and IL-2 therapy in cancer patients (Hibbs et. al., *J. Clin. Invest.*, 89, 867–77, 1992). NOS 2 is implicated in these responses, and thus the possibility exists that a NOS inhibitor would be effective in ameliorating cytokine-induced hypotension. Recent studies in animal models have suggested a role for NO in the pathogenesis of inflammation and pain and NOS inhibitors have been shown to have beneficial effects on some aspects of the inflammation and tissue changes seen in models of inflammatory bowel disease, (Miller et. al., *J. Pharmacol. Exp. Ther.*, 264, 11–16, 1990) and cerebral ischemia and arthritis (Ialenti et. al, Br. J. Pharmacol., 110, 701–6, 1993; Stevanovic-Racic et al, *Arth. & Rheum.*, 37, 1062–9, 1994). Moreover transgenic mice deficient in NOS 1 show diminished cerebral ischemia (Huang et. al, *Science*, 265, 1883–5, 1994) and transgenic mice deficient in NOS 2 exhibit enhanced survivability in a model of LPS-induced shock (MacMicking et al. *Cell* 81, 641–650, 1995) and Wei et al. *Nature* 375, 408–411, 1995)).

Further conditions where there is an advantage in inhibiting NO production from L-arginine include therapy with cytokines such as TNF, IL-1 and IL-2 or therapy with cytokine-inducing agents, for example 5, 6-dimethylxanthenone acetic acid, and as an adjuvant to short term immunosuppression in transplant therapy. In addition, compounds which inhibit NO synthesis may be of use in reducing the NO concentration in patients suffering from inflammatory conditions in which an excess of NO contributes to the pathophysiology of the condition, for example adult respiratory distress syndrome (ARDS) and myocarditis.

There is also evidence that an NO synthase enzyme may be involved in the degeneration of cartilage which takes place in autoimmune and/or inflammatory conditions such as arthritis, rheumatoid arthritis, chronic bowel disease and systemic lupus erythematosis (SLE). It is also thought that an NO synthase enzyme may be involved in insulin-dependent diabetes mellitus. Therefore, a yet further aspect of the present invention provides cyclic amidine derivatives or salts thereof in the manufacture of a medicament for use in cytokine or cytokine-inducing therapy, as an adjuvant to short term immunosuppression in transplant therapy, for the treatment of patients suffering from inflammatory conditions in which an excess of NO contributes to the pathophysiology of the condition.

SUMMARY OF THE INVENTION

The invention disclosed herein encompasses compounds of Formula I

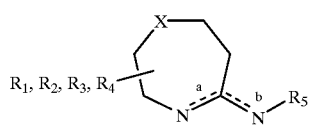

I and pharmaceutically acceptable salts thereof which have been found useful in the treatment of nitric oxide synthase mediated diseases and disorders, including neurodegenerative disorders, disorders of gastrointestinal motility and inflammation. These diseases and disorders include hypotension, septic shock, toxic shock syndrome, hemodialysis, IL-2 therapy such as in in cancer patients, cachexia, immunosuppression such as in transplant therapy, autoimmune and/or inflammatory indications including sunburn, eczema or psoriasis and respiratory conditions such as bronchitis, asthma, oxidant-induced lung injury and acute respiratory distress (ARDS), glomerulonephritis, restenosis, inflammatory sequelae of viral infections, myocarditis, heart failure, atherosclerosis, osteoarthritis, rheumatoid arthritis, septic arthritis, chronic or inflammatory bowel disease, ulcerative colitis, Crohn's disease, systemic lupus erythematosis (SLE), ocular conditions such as ocular hypertension, retinitis and uveitis, type 1 diabetes, insulin-dependent diabetes mellitus and cystic fibrosis. Compounds of Formula I are also usful in the treatment of hypoxia, hyperbaric oxygen convulsions and toxicity, dementia, Alzheimer's disease, Sydenham's chorea, Parkinson's disease, Huntington's disease, amyotrophic lateral sclerosis (ALS), multiple sclerosis, epilepsy, Korsakoff's disease, imbecility related to cerebral vessel disorder, NO mediated cerebral trauma and related sequelae, ischemic brain edema (stroke), sleeping disorders, eating disorders such as anorexia, schizophrenia, depression, pre-menstrual syndrome (PMS), urinary incontinence, anxiety, drug and alcohol addiction, pain, migraine, emesis, tumor growth, immune complex disease, as immunosupressive agents, acute allograft rejection, infections caused by invasive microorganisms which produce NO and for preventing or reversing tolerance to opiates and diazepines.

DETAILED DESCRIPTION OF THE INVENTION

The invention disclosed herein encompasses compounds of Formula I

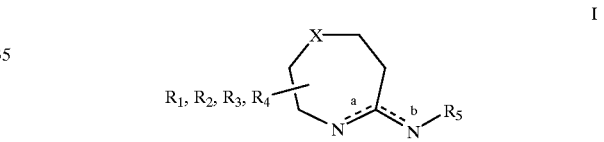

I or a pharmaceutically acceptable salt thereof wherein:
side a or side b has a double bond,
X is selected from 0, $S(O)_m$, NH, and $NR_6$,
  wherein $R_6$ is selected from $C_{1-12}$alkyl, $C_{1-12}$alkyl-carbonyl, $C_{1-12}$aLkyloxy-carbonyl, $C_{1-12}$alkylamino-carbonyl $C_{1-12}$alkyl-sulfonyl and $C_{1-12}$alkylamino-sulfonyl wherein said $C_{1-12}$alkyl group being optionally mono or di-substituted by substituents being independently selected phenyl, $C_{1-6}$alkoxy, amino, and halo;
m is 0, 1 or 2;
$R_1$, $R_2$, $R_3$ and $R_4$ are each independently selected from the group consisting of
  (a) hydrogen,
  (b) $C_{1-12}$alkoxy,
  (c) $C_{1-12}$alkyl-$S(O)_k$ wherein k is 0, 1 or 2,
  (d) mono $C_{1-12}$alkylamino,
  (e) (di-$C_{1-12}$alkyl)amino,
  (f) $C_{1-12}$alkylcarbonyl,
  (g) $C_{1-12}$alkyl,
  (h) $C_{2-12}$alkenyl,
  (i) $C_{2-12}$alkynyl,
  (j) $C_{5-10}$cycloalkyl,
  (k) hetero $C_{5-10}$cycloalkyl, wherein the hetero $C_{5-10}$cycloalkyl optionally contains 1 or 2 heteroatoms selected from S, O and N,
  (l) aryl, selected from phenyl or naphthyl, (m) heteroaryl, wherein heteroaryl is selected from the group consisting of:
(1) benzimidazolyl,
(2) benzofuranyl,
(3) benzooxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(17) isoquinolyl,
(18) tetrazolyl,
(19) thiadiazolyl,
(20) thiazolyl,
(21) thienyl, and
(22) triazolyl,
(n) $C_{1-12}$alkyl-C(O)NH,
(o) $C_{1-12}$alkoxy-C(O)NH,
(p) $C_{1-12}$alkylamino-C(O)NH,
(q) $C_{1-12}$alkyl-S(O)$_2$NH,
(r) $C_{1-12}$alkylamino-C(O),
(s) $C_{1-12}$alkylamino-S(O)$_2$,
(t) aryl-C(O)NH where aryl is selected from phenyl, naphthyl, pyridyl, thienyl, thiazolyl, oxazolyl, imidazolyl, and triazolyl,
(u) aryloxy-C(O)NH where aryl is selected from phenyl, naphthyl, and pyridyl,
(v) phenylamino-C(O)NH,
(w) aryl-S(O)$_2$NH where aryl is selected from phenyl and naphthyl,
(x) aryl-C(O) where aryl is selected from phenyl, naphthyl, pyridyl, thienyl, thiazolyl, oxazolyl, imidazolyl, and triazolyl,
(y) phenylamino-S(O)$_2$,
(z) hydroxy,
(aa) amino,
(ab) oxo,
(ac) C(O)OR$_7$, R$_7$ is selected from hydrogen, phenyl, benzyl, cyclohexyl or $C_{1-6}$alkyl,
each of (b) to (y) being optionally mono or di-substituted, the substituents being independently selected from
(1) hydroxy,
(2) —C(O)OH,
(3) —NR$_7$R$_8$, where R$_8$ is selected from hydrogen, phenyl, benzyl, cyclohexyl or C16alkyl,
(4) —NR$_7$C(O)R$_8$,
(6) —NR$_7$C(O)NHR$_8$,
(5) —NR$_7$C(O)OR$_9$, where R$_9$ is selected from phenyl, benzyl, cyclohexyl or $C_{1-6}$alkyl,
(7) —NR$_7$S(O)$_2$R$_9$,
(8) -OR$_7$,
(9) —C(O)OR$_9$,
(10) —C(O)NR$_7$R$_8$,
(11) —C(O)R$_7$,
(12) —S(O)$_k$R$_7$,
(13) —S(O)$_2$NR$_7$R$_8$,
(14) halo selected from F, Cl, Br and I,
(15) —CF$_3$,
(16) C(=NR$_7$)—NHR$_8$,
(17) hetero $C_{5-10}$ocycloalkyl, wherein the hetero $C_{5-10}$ocycloalkyl optionally contains 1 or 2 heteroatoms selected from S, O and N,
(18) aryl, selected from phenyl or naphthyl,
(19) heteroaryl, wherein heteroaryl is selected from the group consisting of:
(a) imidazolyl,
(b) isooxazolyl,
(c) isothiazolyl,
(d) oxadiazolyl,
(e) oxazolyl,
(f) pyridyl,
(g) tetrazolyl,
(h) thiazolyl,
(i) thienyl, and
(j) triazolyl,
or when two members of the group R$_1$, R$_2$, R$_3$ and R$_4$ including the optional substituents present thereon reside on the same carbon atom of Formula I, or two of the group R$_1$, R$_2$, R$_3$ and R$_4$ including the optional substituents present thereon reside on adjacent atoms of Formula I, said two members may optionally be joined, such that together with the carbon atom to which they are attached there is formed a saturated or unsaturated monocyclic ring of 5, 6 or 7 atoms, said monocyclic ring optionally containing up to three hetero atoms selected from N, O or S,
or when a member of the group R$_1$, R$_2$, R$_3$ and R$_4$ including the optional substituents present thereon resides on an atom adjacent to the N on which R$_6$ resides, said member may optionally be joined with R$_6$, such that together with the N on which R$_6$ resides and the carbon on which said member resides there is formed a saturated or unsaturated monocyclic heterocycle of 5, 6 or 7 atoms, said monocycle optionally containing up to three hetero atoms selected from N, O or S,
R$_5$ is selected from the group consisting of
(a) hydrogen,
(b) linear and branched $C_{1-12}$alkyl, optionally mono or di-substituted, the substituents being independently selected from
(1) hydroxy,
(2) carboxy,
(3) —NR$_7$R$_8$,
(4) —OR$_7$,
(5) —C(O)OR$_7$,
(6) —S(O)$_k$R$_7$,
(7) halo selected from F, Cl, Br and I,
(8) —CF$_3$,
(9) phenyl, optionally mono or di-substituted with hydroxy, halo, $C_{1-4}$alkyl, or $C_{1-4}$alkoxy,
(c) —C(O)NR$_{10}$R$_{11}$, where R$_{10}$ and R$_{11}$ are each independently hydrogen, phenyl, cyclohexyl, —S(O)$_2$NR$_7$R$_8$ or optionally substituted $C_{1-6}$alkyl, wherein the substituent is selected from
(1) —NR$_{12}$R$_{13}$, wherein R$_{12}$ and R$_{13}$ are each independently H, $C_{1-6}$alkyl, phenyl or benzyl,
(2) —OR$_{12}$,
(3) —C(O)OR$_{12}$,
(4) —S(O)$_k$Rl2, where k is 0, 1 or 2,
(5) halo selected from F, Cl, Br and I,
(6) optionally substituted aryl wherein aryl and aryl substituents are as defined above,
(7) optionally substituted heteroaryl wherein heteroaryl and heteroaryl substituents are as defined above, (8) optionally substituted $C_{5-10}$cycloalkyl wherein cycloalkyl and cycloalkyl substituents are as defined above,
(9) hetero $C_{5-10}$cycloalkyl, wherein the hetero$C_{5-10}$-iocycloalkyl optionally contains 1 or 2 heteroatoms selected from S, O and N, (d) —C(O)$R_{11}$,
(e) —C(O)O$R_{11}$,
(f) aryl, selected from phenyl or naphthyl,
(g) cyclohexyl.

Within this embodiment there is a genus of compounds wherein
$R_1$, $R_2$, $R_3$ and $R_4$ are each independently selected from the group consisting of
(a) hydrogen,
(b) hydroxy,
(c) amino,
(d) cyano,
(e) fluoro, chloro, bromo, and iodo,
(f) trifluoromethyl,
(g) $C_{1-6}$alkyl,
(h) $C_{1-6}$alkoxy,
(i) $C_{1-6}$alkylthio,
(j) $C_{1-6}$alkylcarbonyl,
(k) mono- and di-$C_{1-6}$alkylamino,
(l) aryl, where aryl is phenyl and naphthyl,
(m) aryloxy, where aryl is phenyl and naphthyl,
(n) cycloalkyl, wherein the cycloaLkyl is a 5-, 6-, or 7-membered monocyclic ring which optionally contains 1 or 2 heteroatoms selected from S, O, and N, and
(o) heteroaryl, wherein heteroaryl is selected from the group consisting of:
(1) pyridyl,
(2) furanyl,
(3) thienyl,
(4) pyrazinyl,
(5) pyrimidyl,
(6) thiazolyl, and
(7) triazolyl,
each of (g) to (o) being optionally mono- or di-substituted, the substituents being independently selected from
(1) hydroxy,
(2) $C_{1-4}$alkyl,
(3) $C_{1-3}$alkoxy,
(4) amino,
(5) mono- and di-$C_{1-6}$alkylamino,
(6) carboxyl,
(7) $C_{1-3}$alkylthio,
(8) $C_{1-3}$aLkYl-S(O)$_k$-, where k is 1 or 2,
(9) $C_{1-4}$alkoxycarbonyl,
(10) halo selected from fluoro, chloro, bromo, and iodo,
(11) oxo, and
(12) amidino,
$R_5$ is selected from the group consisting of
(a) hydrogen,
(b) $C_{1-6}$alkylcarbonyl,
(c) arylcarbonyl, wherein the aryl group is phenyl,
(d) arylcarbonyl-aminocarbonyl, wherein the aryl group is phenyl and naphthyl,
(e) $R_6R_7N$—$SO_2$—NH—C(=O)-, wherein $R_6$ and $R_7$ are independently selected from the group consisting of
(1) hydrogen,
(2) $C_{1-6}$alkyl,
(3) aryl, wherein the aryl group is selected from phenyl, and
(4) $R_6$ and $R_7$ may be joined together to form a 5-, 6- or 7-membered ring containing 0, 1 or 2 heteroatoms, the heteroatoms being elected from the group of oxygen, sulfur and nitrogen,
each of (b) to (e) being mono- or di-substituted, the substituents being independently selected from
(1) hydroxy,
(2) $C_{1-3}$alkoxy,
(3) amino,
(4) mono- and di-$C_{1-6}$alkylamino,
(5) carboxyl,
(6) $C_{1-3}$alkylthio,
(7) $C_{1-3}$alkyl-S(O)$_k$—, where k is 1 or 2,
(8) $C_{1-4}$alkoxycarbonyl,
(9) halo selected from fluoro, chloro, bromo, and iodo,
(10) oxo, and
(11) amidino.

Within this genus there is a class of compounds wherein
$R_1$, $R_2$, $R_3$ and $R_4$ are each independently selected from the group consisting of
(a) hydrogen,
(b) hydroxy,
(c) amino,
(d) cyano,
(e) fluoro, chloro or bromo,
(f) trifluoromethyl,
(g) $C_{1-4}$alkyl,
(h) $C_{1-4}$alkoxy,
(i) $C_{1-4}$alkylthio, and
(j) mono- and di-$C_{1-4}$alkylamino,
$R_5$ is selected from the group consisting of
(a) hydrogen
(b) $R_6R_7N$—$SO_2$—NH—C(=O)—, optionally mono or di-substituted, wherein $R_6$ and $R_7$ are independently selected from the group consisting of
(1) hydrogen,
(2) $C_{1-4}$alkyl, and
(3) aryl, wherein the aryl group is phenyl, and
said substituents are independently selected from
(1) hydroxy,
(2) $C_{1-3}$alkoxy,
(3) amino,
(4) mono- and di-$C_{1-6}$alkylamino,
(5) carboxyl,
(6) $C_{1-3}$alkylthio, and
(7) halo selected from fluoro, chloro, and bromo.

Within this class there is a sub-class of compounds wherein
$R_2$ is hydrogen or methyl;
$R_4$ is hydrogen or methyl;
$R_1$ and $R_3$ are each independently selected from
(a) hydrogen,
(b) methyl, ethyl, propyl or butyl,
(c) chloro,
(d) —CN, and
(e) —$CF_3$; and
$R_5$ is hydrogen.

Illustrating the invention are:
(a) hexahydro-5-imino-(1H)-1,4-diazepine dihydrochloride,
(b) hexahydro-5-imino-1,4-thiazepine hydrochloride
(c) hexahydro-5-imino-1,4-oxazepine hydrochloride,
(d) hexahydro-5-imino-3-propyl-1,4-thiazepine hydrochloride, (e) hexahydro-5-imino-6-propyl-1,4-thiazepine hydrochloride, (f) hexahydro-5-imino-7-methyl-1,4-thiazepine hydrochloride, (g) hexahydro-5-imino-2-methyl-1,4-thiazepine hydrochloride, (h) hexahydro-5-imino-6-(3-methyl-2-n-butenyl)-1,4-thiazepine hydrochloride, (i) hexahydro-5-imino-3-(3-methyl-2-n-butenyl)-1,4-thiazepine hydrochloride, (j) hexahydro-5-imino-6-(2-methyl-propyl)-1,4-thiazepihe hydrochloride, (k) hexahydro-5-imino-3-(2-methyl-propyl)-1,4-thiazepine hydrochloride, (l) hexahydro-5-imino-6-methyl-1,4-thiazepine hydrochloride, (m) hexahydro-5-imino-3-methyl-1,4-thiazepine hydrochloride, (n) hexahydro-5-imino-3-ethyl-1,4-thiazepine hydrochloride, (o) -hexahydro-5-imino-3-butyl-1,4-thiazepine hydrochloride, (p) hexahydro-5-imino-3-(2-methyl-3-propenyl)-1,4-thiazepine hydrochloride, (q) (±)-trans-decahydro-4-imino-benzo[b]-1,4-thiazepine acetic acid salt., (r) hexahydro-5-imino-3(S)-propyl-1,4-thiazepine acetic acid salt, (s) hexahydro-5-imino-3(R)-propyl-1,4-thiazepine acetic acid salt, (t) hexahydro-5-imino-1-methyl-(1H)-1,4-diazepine hydrochloride, and pharmaceutically acceptable salts thereof.

For purposes of this specification alkyl is defined to include linear, branched, and cyclic structures, with $C_{1-6}$alkyl including methyl, ethyl, propyl, 2-propyl, s- and t-butyl, butyl, pentyl, hexyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$ alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies $-SCH_2CH_2CH_3$.

Heteroaryl includes furan, benzofuran, thiophene, pyrrole, indole, isoxazole, isothiazole, pyrazole, oxazole, benzoxazole, thiazole, imidazole, benzirnidazole, 1,2,3-oxadiazole, 1,2,3-thiadiazole, 1,2,3-triazole, 1,3,4-oxadiazole, 1,3,4-thiadiazole, 1,3,4-triazole, 1,2,5-oxadiazole, 1,2,5-thiadiazole, pyridine, quinoline, isoquinoline, pyridazine, pyrirnidine, pyrazine, 1,2,4-triazine, 1,3,5-triazine, 1,2,4,5-tetrazine, tetrazole, and the like.

As appreciated by those of skill in the art, the depiction

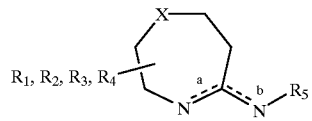

is intented to indicate that substituents $R_1$, $R_2$, $R_3$ and $R_4$ may each independently reside at any available position on the ring structure of FIG. I.

Illustrative of the situation wherein two members of $R_1$, $R_2$, $R_3$ and $R_4$ are joined together to form a ring or one member is joined together with $R_6$ to form a ring include the following:

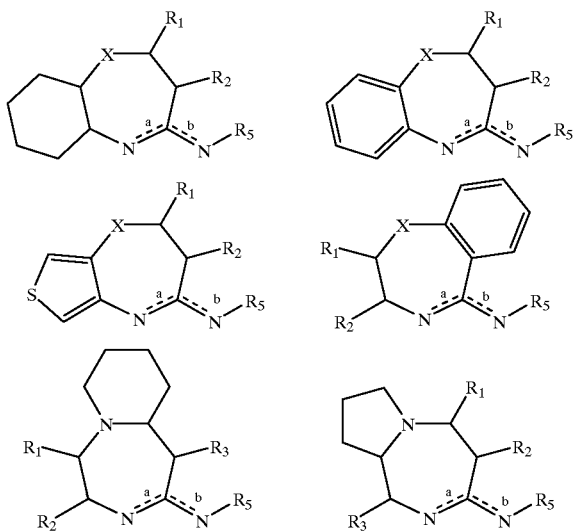

As outlined in the summary of the invention, the compounds of the instant invention are useful in the treatment of a number of NOS implicated diseases. The implication of these diseases is well documented in the literature. For example, with regard to psoriasis, see Ruzicka et. al., J. Invest. Derm., 103: 397 (1994) or Kolb-Bachofen et. al., Lancet, 344: 139 (1994) or Bull, et al., J. Invest. Derm., 103:435(1994); with regard to uveitis, see Mandia et. al., Invest Opthalmol., 35: 3673–89 (1994); with regard to type 1 diabetes, see Eisieik & Leijersfam, Diabetes & Metabolism, 20: 116–22 (1994) or Kroncke et. al., BBRC, 175: 752–8 (1991) or Welsh et. al, Endocrinol., 129: 3167–73 (1991); with regard to septic shock, see Petros et. al., Lancet, 338: 1557–8 (1991), Thiemermann & Vane, Eur. J. Pharmacol., 211: 172–82 (1992), or Evans et. al., Infec. Imm., 60: 4133–9 (1992), or Schilling et. al., Intensive Care Med., 19: 227–231 (1993); with regards to pain, see Moore et. al, Brit. J. Pharmacol., 102: 198–202 (1991), or Moore et. al, Brit. J. Pharmacol., 108: 296–97 (1992) or Meller et. al, Europ. J. Phannacol, 214: 93–6 (1992) or Lee et. al., NeuroReport, 3: 841–4 (1992); with regard to migraine, see Olesen et. al, TIPS, 15: 149–153 (1994); with regard to rheumatoid arthritis, see Kaurs & Halliwell, FEBS Letters, 350: 9–12 (1994); with regard to osteoarthritis, see Stadler et. al, J. Immunol., 147: 3915–20 (1991); with regard to inflammatory bowel disease, see Miller et. al, Lancet, 34: 465–66 (1993) or Miller et. al., J. Pharmacol. Exp. Ther., 264: 11–16 (1993); with regard to asthma, see Hamid et. al., Lancet, 342: 1510–13 (1993) or Kharitonov, et. al., Lancet, 343: 133–5 (1994); with regard to Immune complex diseases, see Mulligan et. al., Br. J. Pharnacol., 107: 1159–62 (1992); with regard to multiple sclerosis, see Koprowski et. al., PNAS, 90: 3024–7 (1993); with regard to ischemic brain edema, see Nagafuji et. al., Neurosci., 147: 159–62 (1992) or Buisson et. al., Br. J. Pharmacol., 106: 766–67 (1992) or Trifiletti et. al., Europ. J. Pharmacol., 218: 197–8 (1992); with regard to toxic shock syndrome, see Zembowicz & Vane, PNAS, 89: 2051–55 (1992); with regard to heart failure, see Winlaw et. al., Lancet, 344: 373–4 (1994); with regard to ulcerative colitis, see Boughton-Smith et. al., Lancet 342: 338–40 (1993); and with regard to atherosclerosis, see White et. al., PNAS, 91: 1044–8 (1994); with regard to glomerulonephritis, see M ühl et. al., Br. J. Pharmcol., 112: 1–8 (1994); with regard to paget's disease and osteoporosis, see Löwick et. al, J. Clin. Invest., 93: 1465–72 (1994) or Evans et al., Clin. Orthopaedics & Related Res., 312: 275–294 (1995); with regard to inflammatory sequelae of viral infections, see Koprowski et. al., PNAS, 90: 3024–7 (1993); with regard to retinitis, see Goureau et. al., BBRC, 186: 854–9 (1992); with regard to oxidant induced lung injury, see Berisha et. al., PNAS, 91, 744–9 (1994); with regard to eczema, see Ruzica, et al., J. Invest. Derm., 103, 395(1994); with regard to acute allograft rejection, see Devlin, J. et al., Transplantation, 58, 592–595 (1994); with regard to infection caused by invasive microorganisms which produce NO, see Chen, Y. and Rosazza, J. P. N., Biochem. Biophys. Res. Comm., 203:1251–1258 (1994); and with regard to tumor growth, see Jenkins et al., PNAS, 92, 4392–4396 (1995).

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic acids or bases including inorganic bases and organic bases. Salts derived from inorganic acids include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The pharmaceutical compositions containing the active ingredient of the instant invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents,-may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For-topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of adrninistration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Assay Protocol for NOS Activity

NOS activity is measured as the formation of L-[2,3,4,5-$^3$H]Citrulline from L-[2,3,4,5-$^3$H]Arginine. The incubation buffer (100 uL) contained; 100 mM TES, pH 7.5, 5 $\mu$M FAD, 5 $\mu$M FMN, 10 $\mu$M BH$_4$, 0.5 mM NADPH, 0.5 mM DTT, 0.5 mg/mL BSA, 2 mM CaC12, 10 ug/mL calmodulin (bovine), 1 $\mu$M L-Arg, 0.2 uCi L-[2,3,4,5-$^3$H] Arg, and the inhibitor in aqueous DMSO (max. 5%). The reaction is initiated by addition of enzyme. Incubations are performed at room temperature for 30 minutes and stopped by the addition of an equal volume of quenching buffer consisting of 200 mM sodium citrate, pH 2.2, 0.02% sodium azide. Reaction products are separated by passing through a cation exchange resin and quantitated as cpm by scintillation counting. Percent inhibition is calculated relative to enzyme incubated without inhibitor according to: % inhibition =100×(cpm L-[2,3,4,5-$^3$H]Cit with inhibitor/cpm L-[2,3,4, 5-$^3$H]Cit without inhibitor).

Illustrative of the utility of the compounds of Formula I is the ability of such compounds to inhibit NO synthase as shown in Table 1 and as measured by the assay described above:

TABLE 1

Inhibition of Nitric Oxide Synthase Isozymes

| Example Number | iNOS (IC$_{50}$, uM) | ecNOS (IC$_{50}$, uM) | ncNOS (IC$_{50}$, uM) |
|---|---|---|---|
| 1 | >50 | >50 | >50 |
| 2 | <10 | >10 | <10 |
| 3 | <50 | <50 | <10 |
| 4 | <1 | <50 | <10 |
| 5 | >50 | >50 | >50 |
| 6 | <10 | <10 | <1 |
| 7 | <10 | <10 | <1 |
| 8 | >50 | >50 | >50 |
| 9 | <1 | >50 | <50 |
| 10 | <50 | >50 | >50 |
| 11 | <1 | >50 | <10 |
| 12 | >50 | <50 | <10 |
| 13 | <1 | <10 | <10 |
| 14 | <1 | <50 | <10 |
| 15 | <1 | >50 | <10 |
| 16 | <1 | <50 | <10 |
| 17 | >50 | >50 | >50 |
| 18 | <1 | <10 | <1 |

TABLE 1-continued

Inhibition of Nitric Oxide Synthase Isozymes

| Example Number | iNOS (IC$_{50}$, uM) | ecNOS (IC$_{50}$, uM) | ncNOS (IC$_{50}$, uM) |
|---|---|---|---|
| 19 | <10 | <50 | <10 |
| 20 | <50 | >50 | >50 |

Methods of Synthesis

The compounds of the present invention can be prepared according to the following methods.

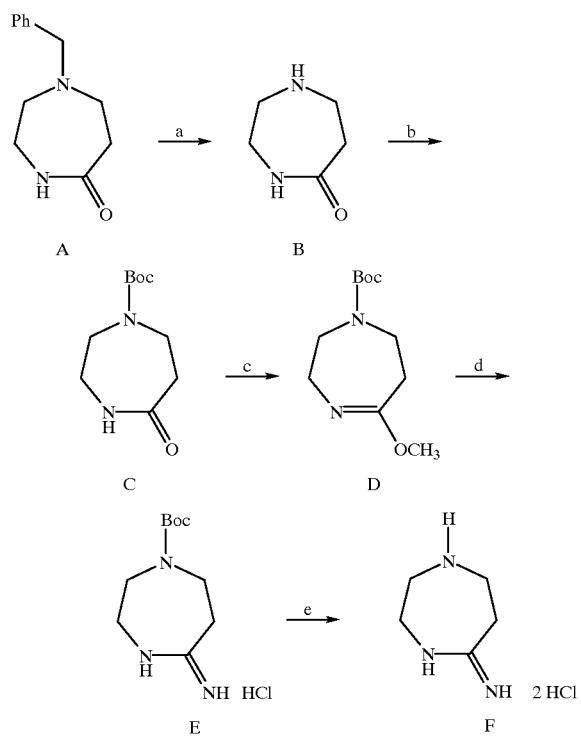

Reaction conditions:
a) H$_2$ 40 psi, Pd(OH)$_2$/C, EtOH, HOAc, 4 hr; b) (t-C$_4$H$_9$O$_2$C)$_2$O, NaCl, NaOH, CHCl$_3$, reflux, 4hr; c) (CH$_3$)$_3$OBF$_4$, CH$_2$Cl$_2$, RT, overnight; d) NH$_4$Cl, EtOH, reflux, 4 hr; e) HCl, ethyl acetate, RT, overnight.

As shown in Scheme 1, hexahydro-1-(phenylmethyl)-(5H)-1,4-diazepin-5-one A (prepared as described by T. Iira, CAS 84:31153r, 83:179149u) is reacted under hydrogen atmosphere at 40 psi in the presence of palladium hydroxide catalyst in ethanol and acetic acid to give hexahydro-5H-1,4-diazepin-5-one B as the acetic acid salt. Reaction with di-t-butyl dicarbonate in the presence of sodium chloride and sodium hydroxide gives 1-(tert-butyloxycarbonyl)-hexahydro-(5H)- 1,4-diazepin-5-one C. The imino ether D is formed from C by reaction with Meerwein's salt (trimethyloxonium fluoroborate). The amidine E is obtained by reaction of D with ammonium chloride in refluxing ethanol. The amine protecting group in E is removed by reaction with hydrogen chloride in ethyl acetate to give the desired amidine F as the dihydrochloride salt.

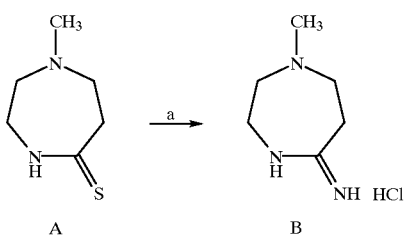

Reaction conditions:
a) NH$_3$, HgCl$_2$, THF

An alternative preparation of the amidine functionality is shown in Scheme 2. A thioamide A is reacted directly with ammonia in the presence of mercuric chloride to give the 5-imino-1,4-diazepine B.

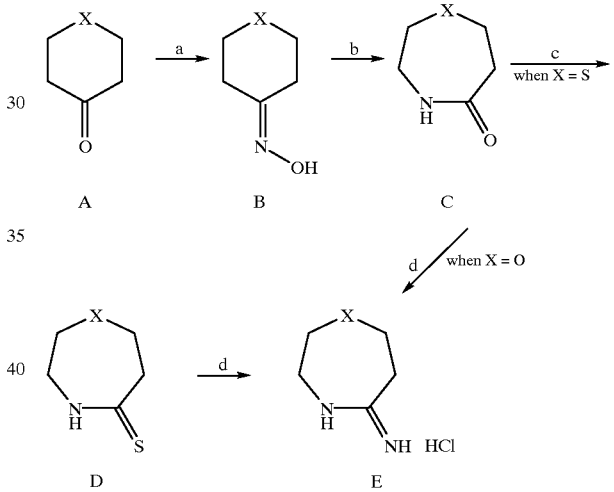

Reaction conditions:
a) NH$_2$OH—HCl, NaOH, EtOH; b) n-BuLi, TsCl; Et$_3$N, aq. dioxane; c) Lawesson's reagent, tol, 90° C.; d) Me$_3$OBF$_4$, iPr$_2$NEt, CH$_2$Cl$_2$; NH$_4$Cl, EtOH, reflux 1,4—Oxa- and thiazepine analogs are prepared by 5 methodology outline in Scheme 3. A ketone derivative A is converted to its corresponding oxime B by reaction with hydroxylamine in ethanol. Ring expansion of B via a Beckmann rearrangement of the O-tosyl-oxime formed by reaction of B with with butyl lithium and p-toluenesulfonyl chloride gives hexahydro-1,4-heteroazepin-5-one C. When X=S, the amide in C is converted to the thioamide D by reaction with Lawesson's reagent. Reaction of D with Meerwein's salt to form the imino-thioether followed by reaction with ammonium chloride gives the hexahydro-5-imino-1, 4heteroazepine E. Alternatively, when X=O in C, reaction with Meerwein's salt followed by ammonium chloride gives E directly.

Scheme 4

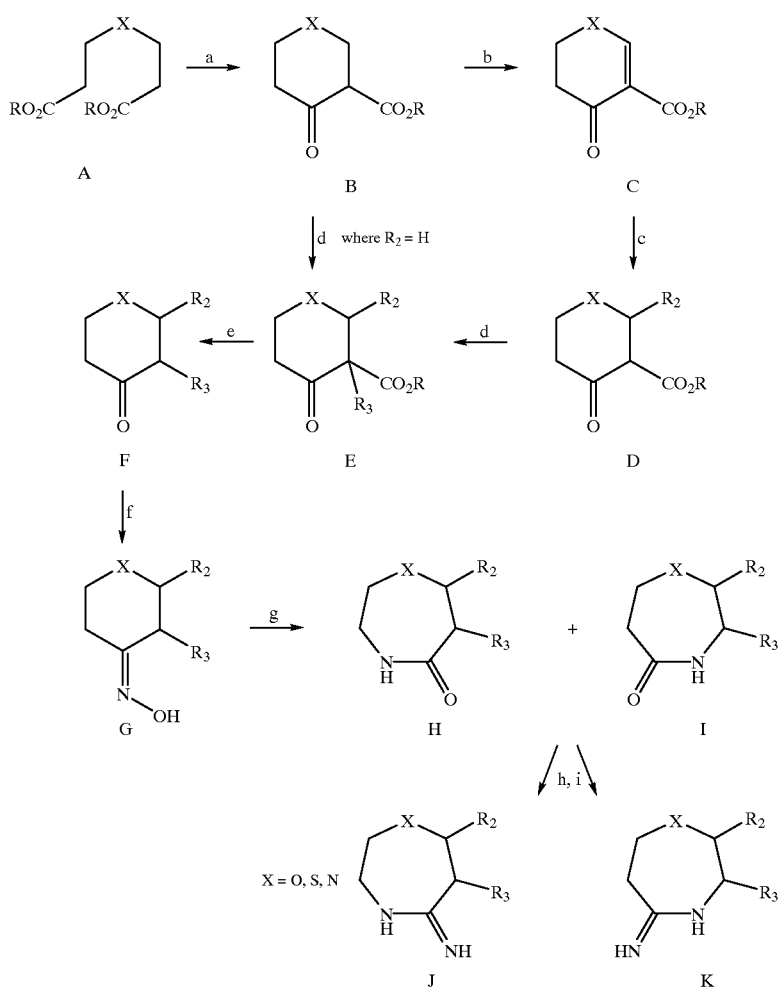

Reaction conditions:
a) NaOR, Et$_2$O; b) MnO$_2$, CHCl$_3$, reflux; c) Cu$_2$I$_2$, (R$_2$)Li, CH$_3$SCH$_3$; d) NaH, (R$_3$)X, DMF; e) when R = allyl, (Ph$_3$P)$_4$Pd(0), morpholine, THF, f) H$_2$NOH—HCl; NaOH, EtOH; g) n-BuLi, TsCl, Et$_2$O; Et$_3$N, aq. dioxane; h) Lawesson's reagent; separate positional isomers; i) Me$_3$OBF$_4$, iPr$_2$NEt, CH$_2$Cl$_2$; NH$_4$Cl, EtOH.

More highly substituted hexahydro-5-imino-1,4-heteroazepines may be prepared according to methodology outlined in Scheme 4. Diester A is cyclized via a Diechinann condensation to keto-ester B. Treatment of B with a strong base such as sodium hydride followed by addition of an alkylating agent such as n-propyl iodide will give E (where R$_2$ is hydrogen and R$_3$ is n-propyl). Alternatively, keto-ester B may be oxidized by manganese dioxide to form the α,β-unsaturated keto-ester C. A substituent R$_2$ is introduced via a Michael reaction with an organo-cuprate reagent to form D. Alkylation of D with (R$_3$)X in the presence of a strong base will form E (R$_2$ and R$_3$ are not hydrogen). Deesterification-decarboxylation of E will form F. By procedures outlined in Scheme 3, F is converted to amides H and I via Beckmann rearrangement of oxime G. Since the Beckmann rearrangement can occur with migration to either side of the oxime, the two amides H and I may be formed. These amides H and I may be separated chromatographically at this point or, alternatively, may be subsequently converted to their respective thioamides by reaction with Lawesson's reagent and then separated. Reaction of the thioamides from H and I with Meerwein's salt followed by treatment with ammonium chloride will give substituted hexahydro-5-imino-1,4-heteroazepines I and K. When X is nitrogen, a appropriate amine protecting group (eg., tert-butyloxycarbonyl) may be employed in the reaction sequence.

Scheme 5

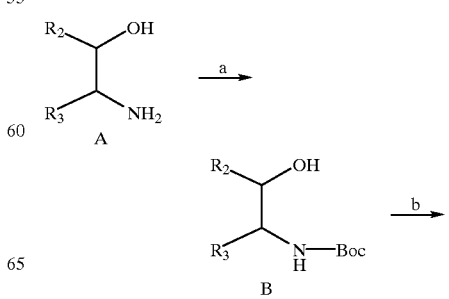

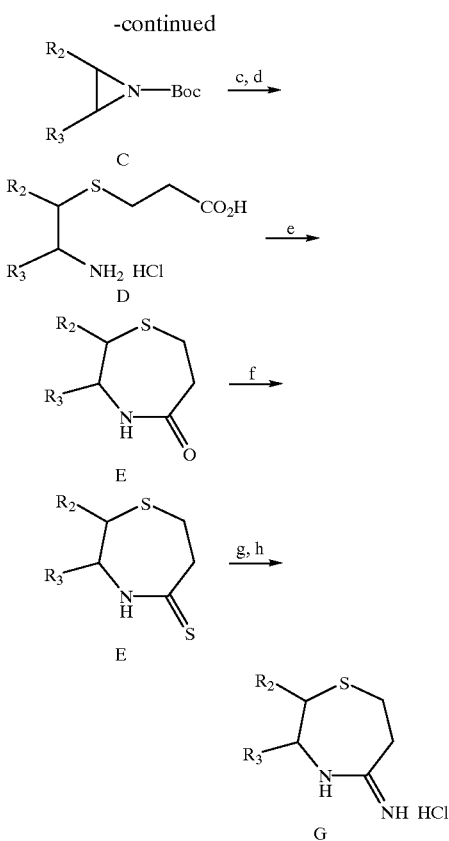

More highly substituted hexahydro-5-imino-1,4-heteroazepines may also be prepared according to methodology outlined in Scheme 5. Briefly, the amine functionality in aminoalcohol A is protected to give B. Mitsunobu conditions will cyclize B to form aziridine C. The aziridine ring in C is opened with P-mercaptopropionic acid followed by treatment with. hydrochloric acid in ethyl acetate to yield amino acid D. Reaction of D under standard peptide bond forming reactions gives lactam E. Reaction with Lawesson's reagent gives the thiolactam F which is converted to 5-imino-1,4-thiazepine G by previously described conditions.

The invention will now be illustrated by the following non-limiting examples in which, unless stated otherwise:

all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 400 MHz or 500 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLE 1

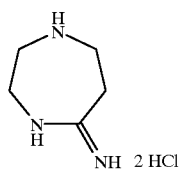

Hexahydro-5-imino-(1H-1,4-diazepine Dihydrochloride

Step A: Hexahydro-(5H)-1,4-diazepine-5-one Acetic Acid Salt.

1-Benzylhexahydro-(5H)-1,4-diazepine-5-one (1.5 g, 7.34 mmol) was dissolved in 12 mL of ethanol and 6 mL of acetic acid. After addition of 150 mg of 20% palladium hydroxide on carbon, the mixture was shaken under 40 psi of hydrogen for 4 h. The resulting mixture was centrifuged and the supernatant was filtered through a 0.45 micron membrane filter. The catalyst was washed with ethanol (3×10 mL), and the combined filtrate was concentrated in vacuo to give a yellow oil which began to crystallize. Swirling with 2 mL of methanol and 1 mL of ethyl acetate facilitated the crystallization, and evaporation of the solvent in vacuo gave 1.23 g (96%) of hexahydro-(5H)-1,4-diazepin-5-one acetic acid salt as light yellow crystals.

$^1$H NMR (400 MHz, CD$_3$OD): δ 3.44–3.40 (m, 2H), 3.19–3.15 (m, 2H), 3.15–3.11 (m, 2H), 2.74–2.70 (nm, 2H), 1.94 (s, 3H). Mass spectrum: m/z=115 (M+1, 100%).

Step B: 1-(tert-Butoxycarbonyl)hexahydro-(5H)-1,4-diazepin-5-one.

A mixture of hexahydro-(5H)-1,4-diazepin-5-one acetic acid salt (200 mg, 1.15 mmol), di-tert-butyldicarbonate (277 mg, 1.27 mmol) and sodium chloride (460 mg, 7.93 mmol) in 2.0 mL of chloroform was stirred and 2.5 N aqueous sodium hydroxide (460 μL, 1.15 mmol) was added. The mixture was heated to reflux for 4 h, and then extracted with 3×10 mL of ethyl acetate. The combined ethyl acetate extracts were dried over anhydrous sodium sulfate, decanted and evaporated in vacuo to give 219 mg (89%) of 1-(tert-butoxycarbonyl)hexahydro-(5H)-1,4-diazepin-5-one as a white solid.

1H NMR (400 MHz, CD$_3$OD): δ 3.60–3.53 (m, 4H), 3.28–3.25 (m, 2H), 2.61–2.56 (m, 2H), 1,47 (s, 9H). Mass spectrum: m/z=215 (M+1, 100%). Anal. calcd for C$_{10}$H$_{18}$N$_2$O$_3$: C, 56.32; H, 8.04; N, 13.14. Found: C, 55.92; H, 8.48; –N, 13.00.

Step C: 1-(tert-Butoxycarbonyl)-2,3,6.7-tetrahydro-5-methoxy-(1H-1,4-diazepine.

Trimethyloxonium tetrafluoroborate (Meerwein's salt) (141 mg, 0.94 mmol) was added in one portion to a solution of 1-(tert-butoxycarbonyl)hexahydro-(5H)-1,4-diazepin-5-one (200 mg, 0.94 mmol) in 2.0 mL of anhydrous methylene chloride. The mixture was stirred overnight at room temperature. The reaction mixture was partitioned between 10 mL of saturated aqueous sodium bicarbonate and 20 mL of ethyl acetate. The organic layer was separated and the aqueous layer was extracted with 3×10 mL of ethyl acetate. The combined ethyl acetate layers were washed with saturated aqueous sodium bicarbonate and saturated aqueous sodium chloride. After drying over anhydrous sodium sulfate, the organic solution was concentrated in vacuo to give 180 mg (85%) of 1-(tert-butoxycarbonyl)-2,3,6,7-tetrahydro-5-methoxy-(1H)-1,4-diazepine as a yellow liquid.

$^1$H NMR(400 MHz, CD$_3$OD): δ 3.58 (s, 3H), 3.53–3.45 (m, 6H), 2.63–2.59 (m, 2H), 1.46 (s, 9H). Mass spectrum: m/z=129.

Step D: 1-(tert-Butoxycarbonyl)-hexahydro-5-imnino-(1H)-1,4-diazepine Hydrochloride .

A mixture of 1-(tert-butoxycarbonyl)-2,3,6,7-tetrahydro-5-methoxy-(1H)-1,4-diazepine (170 mg, 0.75 mmol) and ammonium chloride (40.1 mg, 0.75 mmol) in 2.0 mL of anhydrous ethanol was refluxed for 3 h. The solvent was then removed in vacuo and residue was triturated with 3×10 mL of ether to give 174 mg of 1-(tert-butoxycarbonyl)-hexahydro-5-imino-(1H)-1,4-diazepine hydrochloride as a light yellow solid.

$^1$H NMR (400 MHz,CD$_3$OD): δ 3.71–3.65 (m, 2H), 3.63–3.57 (m, 2H), 3.55–3.50 (m, 2H), 2.90–2.86 (m, 2H), 1.47 (s, 9H). Mass spectrum: m/z=214 (M+1, 100%).

Step E: Hexahydro-5-Imino-(1H)-1,4-diazepine Dihydrochloride.

Hydrogen chloride gas (2.0 g, 55 mmol) was bubbled into 15 mL of ethyl acetate at 0° C. over 3 min. 1-(tert-Butoxycarbonyl)-5-iminohexahydro-(1H)-1,4-diazepine hydrochloride (85 mg, 0.34 mmol ) was added and mixture was stirred at room overnight. Removal of solvent and hydrogen chloride in vacuo gave 60 mg (95%) of hexahydro-5-imino-(1H)-1,4-diazepine dihydrochloride as a yellow solid.

$^1$H NMR (400 MHz, CD$_3$OD): δ 3.84–3.80 (m, 2H), 3.55–3.50 (m, 2H), 3.43–3.39 (m, 2H), 3.21–3.16 (m, 2H). Mass spectrum: m/z=114 (M-2HCl+1, 100%). Anal. calcd for C$_5$H$_{13}$N$_3$C$_{12}$: C, 32.27; H, 7.04; N, 22.58; Cl, 38.10. Found: C, 32.09; H, 7.04; N, 21.67; Cl, 38.05.

EXAMPLE 2

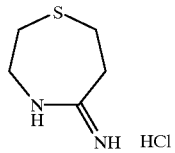

Hexahydro-5-imino-1,4-thiazepine Hydrochloride

Step A: 4-Oximino-tetrahydrothiopyran

To a stirring solution of solution of tetrahydrothiopyran-4-one (4.9 g, 42.1 mmol) and hydroxylarnine hydrochloride (5.9 g, 84 mmol) in 35 mL of ethanol at 0° C. was added a solution of sodium hydroxide (3.38 g, 84.5 mmol) dissolved in 13 mL water. The reaction mixture was warmed to room temperature and stirred for an additional 2 h. The ethanol was removed in vacuo and the aqueous solution extracted with ether (2×250 mL). The etheral layer was washed with with water, saturated sodium chloride solution and dried over anhydrous magnesium sulfate. The solvent was evaporated to give crude oxime which was recrystallized from hexane/ether to give 4. 66 g of 4-oximino-tetrahydrothiopyran.

1H NMR (500 MHz, CDCl$_3$): δ 9.43 (brs, 1H), 2.86 (m, 2H), 2.78(m, 2H), 2.73 (m, 2H), 2.56 (m, 2H). $^{13}$C NMR (125 MHz, CDCl$_3$): δ 158.24, 33.94, 29.75, 28.38, 26.78.

Step B: Tetrahydro-(2H)-1,4-thiazepin-5-one

To a solution of 4-oximino-tetrahydrothiopyran (1.0 g, 7.6 mmol) in 20 mL of dry ether under nitrogen atmosphere at 0° C. was added n-butyllithium (5.0 mL of a 1.6 M solution in hexane, 8.0 mmol). The resulting white suspension was stirred at 0° C. for one hour at which point a solution of p-toluenesulfonyl chloride (1.52 g, 8.0 mmol) in 10 mL ether was added and the reaction mixture stirred for 4 h at 5° C. The solvent was removed in vacuo and then the residue was treated with 20 mL of 70% dioxane containing five drops of triethylamine and stirred for 24 h at room temperature. The solvent was removed in vacuo and the residue was extracted with methylene chloride. The methylene chloride layer was washed with water, saturated sodium chloride and dried over anhydrous magnesium sulfate. The solvent was removed in vacuo and the product purified by flash column chromatography on silica gel eluted with hexane/ethyl acetate (7 :3) to give 0.13 g of hexahydro-(1H)-1,4-thiazepin-5-one.

$^1$H NMR (500 MHz, CDCl$_3$): δ 6.92 (brs, 1H), 3.61 (m, 2H), 2.92(m, 2H), 2.74 (m, 2H), 2.70 (m, 2H). $^{13}$C NMR (125 MHZ, CDCl$_3$): δ 177.76, 45.88, 40.95, 31.54, 24.61.

Step C: Tetrahydro-(2H)-1,4-thiazepin-5-thione

To a solution of tetrahydro-(2H)-1,4-thiazepin-5-one (0.335 g, 2 mmol) in 5 mL of dry toluene was added Lawesson's reagent [2,4-bis(4-methoxyphenyl)-1,3-dithia-2,4-diphosphetane-2,4-disulfide] (0.971 g , 2.4 mmol) and the mixture was stirred at 90° C. for 30 mins. Evaporation of the solvent in vacuo followed by purification by flash column chromatography on silica gel eluted with methylene chloride: ethyl acetate (19:1) gave 0.365 g of tetrahydro-(2H)-1,4-thiazepin-5-thione.

1H NMR (500 MHz, CDCl$_3$): δ 9.19 (brs, 1H), 3.80 (m, 2H), 3.44 (m, 2H), 2.78 (m, 2H), 2.71 (m, 2H). $^{13}$C NMR (125 MHZ, CDCl$_3$): δ 208.90, 50.39, 49.02, 29.54, 25.86.

Step D: Hexahydro-5-imino-1,4-thiazepine Hydrochloride

To a solution of tetrahydro-(2H)-1,4-thiazepin-5-thione (90 mg, 0.5 mmol) in 2 mL of dry methylene chloride at room temperature was added trimethyloxonium tetrafluoroborate (Meerwein's salt) (88 mg, 0.6 mmol) followed by diisopropylethylamine (77 mg, 0.6 mmol). The resulting mixture was stirred at room temperature for 2 h. The methylene chloride layer was washed with water, saturated sodium chloride solution and dried over anhydrous magnesium sulfate. The solvent was removed in vacuo to give the crude imino-ether which was subsequently treated with ammonium chloride (0.017 g) in 3 mL of ethanol and heated at 80° C. for 15 h. Evaporation of ethanol followed by trituration of the oil with ethyl acetate and ether gave 53 mg of hexahydro-5-imino-1,4-thiazepine hydrochloride as a white solid.

$^1$H NMR (500 MHz, D$_2$O): δ 3.81 (m, 2H), 3.11 (m, 2H), 2.84 (m, 2H), 2.76 (m, 2H). $^{13}$C NMR (125 MHz, D$_2$O): δ 46.88, 35.52, 28.84, 23.74. Mass spectrum: m/z=131 (M+1).

EXAMPLE 3

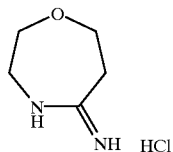

Hexahydro-5-imino-1,4-oxazepine Hydrochloride.

Step A: 4-Oximino-tetrahydropyran

Employing the procedure described in Example 2, step A, tetrahydropyran-4-one was converted to 4-oximino-tetrahydropyran.

$^1$H NMR (500 MHz, CDCl$_3$): δ 3.82 (m, 2H), 3.77 (m, 2H), 2.68 (m, 2H), 2.39 (m, 2H).

Step B: Tetrahydro-(2H)-1,4-oxazepin-5-one

Employing the procedure in Example 2, step B, 4-oximino-tetrahydropyran was converted to tetrahydro-(2H)-1,4-oxazepin-5-one.

$^1$H NMR (500 MHz, CDCl$_3$): δ 7.07 (brs, 1H), 3.79 (m, 2H), 3.75(m, 2H), 3.34 (m, 2H), 2.69 (m, 2H). 13C NMR (125 MHZ, CDCl$_3$): δ 177.94, 71.61, 65.52, 44.74, 41.01.

Step C: Hexahydro-5-imino-1,4-oxazepine, Hydrochloride

Employing the procedure in Example 2, step D, tetrahydro-(2H)-1,4-oxazepin-5-one was reacted with Meerwien's salt and ammonium chloride to form-hexahydro-5-imino-1H-1,4-oxazepine, hydrochloride.

1H NMR (500 MHz, D$_2$O): δ 3.89 (m, 2H), 3.80 (m, 2H), 3.60 (m, 2H), 2.96 (m, 2H). $^{13}$C NMR (125 MHz, D$_2$O): δ 69.54, 64.92, 46.12, 35.42. MS: m/z=115.1 (M+).

EXAMPLE 4

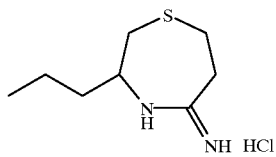

Hexahydro-5-imino-3-propyl-1,4-thiazepine Hydrochloride

Step A: Tetrahydrothiopyran-4-one-3-carboxylic Acid, Allyl Ester.

A mixture of 3,3'-thiodipropionic acid (17.82 g, 10 mmol), allyl alcohol (20.4 mL, 30 mmol) and p-toluenesulfonic acid (0.750 g) in 100 mL of toluene was refluxed for 8 h in a Dean-Stark apparatus to azeotropically remove water. The reaction mixture was quenched with saturated solution of sodium bicarbonate and the toluene layer was separated and washed with saturated sodium chloride solution and dried over anhydrous magnesium sulfate. The solvent was removed in vacuo and gave approximately 20 g of crude 3,3'-thiodipropionic acid, diallyl ester. This material was sufficiently pure by NMR and was used in the subsequent reaction.

To a mixture of sodium hydride (60% in oil, 1.6 g, 38.7 mmol) in 10 mL of dry ether at room temperature was added allyl alcohol (2.25g, 38.7 mmol) in a dropwise manner. The resultant mixture was stirred for 15 min. A solution-of 3,3'-thiodipropionic acid, diallyl ester (5.0 g, 19.3 mmol) in 10 mL ether was slowly added and the mixture refluxed for 5 h. The reaction was cooled to room temperature and then quenched with water and the pH adjusted to 4 with IN HCl. The ether layer was separated and the aqueous layer was extracted with ether (2×100 mL). The combined etheral layer was washed with sautrated sodium chloride solution and dried over anhydrous magnesium sulfate. The solvent was evaporated and the residue purified by flash column chromatography on silica gel eluted with hexane: ether (9 :1) to give 2.57 g of tetrahydrothiopyran-4-one-3-carboxylic acid, allyl ester.

$^1$H NMR (500 MHz, CDCl$_3$): δ 12.48 (s, 1H), 5.95 (m, 1H), 5.35 (m, 2H), 4.68 (m, 2H), 3.38 (s, 2H), 2.78 (t, J=6 Hz, 2H), 2.60 (t, J=6.1 Hz, 2H). $^{13}$C NMR (125 MHZ, CDCl$_3$): δ 172. 80, 131.91, 118.48, 65.32, 30.95, 24.75, 23.58.

Step B: 3-Propyl-tetrahydrothiopyran-4-one-3-carboxylic Acid Allyl Ester.

A solution of tetrahydrothiopyran-4-one-3-carboxylic acid, allyl ester (1.0 g, 5 mmol) in 1 mL of dimethylformamide was added to a stirred mixture of sodium hydride (60% in oil, 0.22 g, 5.5 mmol) and 1-iodopropane (0.934 g, 5.5 mmol) in 2.5 mL of dimethylformamide at 0° C. The reaction mixture was warmed to room temperature and stirred overnight. The reaction mixture was diluted with water and extracted with ether.

The etheral layer was washed with saturated sodium chloride solution and dried over anhydrous magnesium sulfate. The solvent was removed in vacuo and the residue purified by flash column chromatography on silica gel eluted with hexane: ether (19: 1) to give 0.277 g of 3-propyl-tetrahydrothiopyran-4-one-3-carboxylic acid, allyl ester.

$^1$H NMR (500 MHz, CDCl$_3$): δ 5.93 (m, 1H), 5.27–5.38 (m, 2H), 4.70(m, 2H), 3.33–2.73 (m, 6H), 1.96–1.20(m, 4H), 0.93 (t, J=6.3 Hz, 3H). 13C NMR (125 MHZ, CDCl$_3$): δ 205.44, 170.83, 131.36, 119.10, 66.05, 63.14, 43.33, 38.66, 36.66, 30.93, 18.01, 14.48.

Step C: 3-Propyl-tetrahydrothiopyran-4-one.

To a stirred solution of 3-propyl-tetrahydrothiopyran-4-one-3-carboxylic acid, allyl ester (0.272 g, 1.1 mmol) in 5.0 mL dry tetrahydrofuran at room temperature was successively added morpholine (0.979 g, 1.12 mmol) followed by tetrakis(triphenylphosphine)palladium(0) (0.064 g, 0.055 mmol). Stirring was continued until the thin layer chromatography indicated the completion of reaction at which point the reaction mixture was evaporated and the crude product was purified by flash column chromatography on silica gel eluted eluted with hexane: ether (19: 1) to give 0.163 g of 3-propyl-tetrahydrothiopyran-4-one.

$^1$H NMR (500 MHz, CDCl$_3$): δ 3.02–2.94 (m, 7H), 1.88–1.29 (m, 4H), 0.93 (t, J=7.1 Hz, 3H). $^{13}$C NMR (125 MHZ, CDCl$_3$): δ 210.61, 52.77, 43.82, 35.92, 31.58, 31.06, 20.19, 14.13.

Step D: 4—Oximino-3-propyl-tetrahydrothiopyran.

Employing the procedure described in Example 2, step A, 3-propyl-tetrahydrothiopyran-4-one was reacted with hydroxylamine hydrochloride to form 4-oximino-3-propyl-tetrahydrothiopyran and was used directly in the subsequent reaction.

Step E: Tetrahydro-3-propyl-(2H)-1,4-thiazepin-5-one and tetrahydro-6-propyl-(2H)-1,4-thiazepin-5-one.

Employing the procedure described in Example 2, step B, 4-oximino-3-propyl-tetrahydrothiopyran was converted to a 3:1 mixture of tetrahydro-3-propyl-(2H)-1,4-thiazepin-5-one and tetrahydro-6-propyl-(2H)-1,4-thiazepin-5-one.

Step F: Tetrahydro-3-propyl-(2H)-1,4-thiazepin-5-thione.

Employing the procedure described in Example 2, step C, the mixture of tetrahydro-3-propyl-(2H)-1,4-thiazepin-5-one and tetrahydro-6-propyl-(2H)-1,4-thiazepin-5-one was reacted with Lawesson's reagent to yield the corresponding thioamides. The 3-n-propyl isomer was isolated and purified by flash column chromatography on silica gel eluted with methylene chloride: hexanes (1:1) to yield tetrahydro-3-propyl-(2H)-1,4-thiazepin-5-thione as a single compound.

$^1$H NMR (500 MHz, CDCl$_3$): δ 8.06 (brs, 1H), 3.95 (m, 1H), 3.58 (m, 1H), 3.30 (m, 1H), 2.85 (m, 1H), 2.73 (m, 2H), 2.56(m, 1H), 1.71–1.42 (m, 4H), 0.97 (t, J=7.3 Hz, 3H). $^{13}$C NMR (125 MHZ, CDCl$_3$): δ 208.08, 61.95, 48.61, 37.70, 34.41, 25.75, 19.24, 13.68.

Step G: Hexahydro-5-imino-3-propyl-1,4-thiazepine Hydrochloride.

Employing the procedure described in Example 2, step D, tetrahydro-3-propyl-(2H)-1,4-thiazepin-5-thione was reacted with Meerwein's salt and ammonium chloride to yield hexahydro-5-imino-3-propyl-1,4-thiazepine, hydrochloride.

$^1$H NMR (500 MHz, CD$_3$OD): δ 3.93 (m, 2H), 3.23–2.62 (m, 6H), 1.68–1.47(m, 4H), 0.98 (t, 3H, J=7 Hz). $^{13}$C NMR (125 MHZ, CD$_3$OD): δ 170.96, 58.65, 36.54, 34.99, 34.10, 23.36, 18.87, 12.68. MS: m/z=173.1 (M+1).

EXAMPLE 5

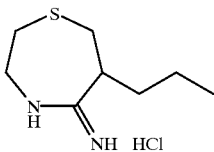

Hexahydro-5-imino-6-propyl-1,4-thiazepine Hydrochloride

The 6-propyl thioamide isomer isolated from Example 4, Step F was reacted with Meerwein's salt and ammonium chloride according to the procedure described in Example 2, Step D to yield hexahydro-5-imino-6-propyl-1,4-thiazepine, hydrochloride.

$^1$H NMR (500 MHz, CD$_3$OD) 3.75 (m, 2H), 3.18 (m, 1H), 2.95 (dd, 1H), 2.82 (m, 1H), 2.73 (m, 2H), 1.87 (m, 2H), 1.50 (m, 1H), 1.39 (m, 1H), 0.99 (t, 3H). Mass spectrum: m/z=173 (M+1)

EXAMPLE 6

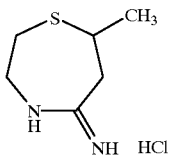

Hexahydro-5-imino-7-methyl-1,4-thiazepine Hydrochloride

Step A: 2,3-Dihydrothiopyran-4-one-3-carboxylic acid, allyl ester.

To a solution of tetrahydrothiopyran-4-one-3-carboxylic acid, allyl ester (Example 4, step A) (2.3 g, 11.5 mmol) in 100 mL dry chloroform at room temperature was added activated manganese dioxide (10 g, 115 mmol) and the resulting mixture was refluxed for 5 h. The reaction mixture was filtered and evaporated. The the remaining residue was purified by flash column chromatography on silica gel eluted with hexane:ethyl acetate (7:3) to give 2,3-dihydrothiopyran-4-one-3-carboxylic acid, allyl ester (0.988 g).

$^1$H NMR (500 MHz, CDCl3): δ 8.49 (s, 1H), 5.97 (m, iH), 5.41–5.25 (m, 2H), 4.70 (m, 2H), 3.29 (m, 2H), 2.82 (m, 2H). $^{13}$C NMR (125 MHZ, CDCl$_3$): δ 189.26, 162.68, 156.42, 131.97, 125.20, 118.61, 65.75, 37.83, 27.29.

Step B: 2-Methyl-tetrahydrothiopyran-4-one-3-carboxylic Acid, Allyl Ester.

To a stirring solution of methyl cuprate in dimethylsulfide (prepared from 1.05 g copper (I) iodide/4.0 mL dimethylsulfide and 4.0 mL methyllithium/ether at −78° C.) at −78° C. was added a solution of 2,3-dihydrothiopyran-4-one-3-carboxylic acid, allyl ester (0.910 g, 4.6 mmol) in dimethylsulfide (5 mL). The resulting yellow-colored solution was stirred for 30 min. at the same temperature. The reaction mixture was quenched with a saturated solution of ammonium chloride and ammonia solution and then warmed to room temperature for and 1 h. The reaction mixture was added to ether (100 mL) and the etheral layer washed with saturated sodium chloride solution and dried over anhydrous magnesium sulfate. The solvent was evaporated and the product purified by flash column chromatography on silica gel eluted with hexane:ether (4:1) to give 2-methyl-tetrahydrothiopyran-4-one-3-carboxylic acid, allyl ester (0.794 g) as a 7:3 mixture of enol : keto tautomers.

$^1$H NMR (500 MHz, CDCl$_3$): δ 12.67 (s, 1H), 5.94 (m, 1H), 5.35–5.27 (m, 2H), 4.70 (m, 2H), 3.09–2.50(m, 6H), 1.52 (d, J=6.9 Hz, 3H). $^{13}$C NMR (125 MHZ, CDCl$_3$): δ 173.02, 131.86, 119.50, 66.71, 65.33, 42.66, 30.76, 23.95, 20.02.

Step C: 2-Methyl-tetrahydrothiopyran-4-one

Employing the procedure described in Example 4, step C, 2-methyl-tetrahydrothiopyran-4-one-3-carboxylic acid, allyl ester was decarboxylated to form 2-methyl-tetrahydrothiopyran-4-one.

Step D: Hexahydro-5-imino-7-methyl-1,4-thiazepine Hydrochloride.

Employing the procedures described in Example 4, steps D through G, 2-methyl-tetrahydrothiopyran-4-one was converted to hexahydro-5-imino-7-methyl-1,4-thiazepine, hydrochloride $^1$H NMR (500 MHz, D$_2$O): δ 3.78 (d, 1H, J=15 Hz), 3.62 (dd, 1H, J=15, 7 Hz), 3.05 (m, 2H), 2.87 (m, 2H), 2.10 (m, 1H), 1.21 (d, 3H, J=7 Hz). $^{13}$C NMR (125 MHz, CD$_3$OD): δ 51.87, 36.76, 34.73, 22.12, 17.34. Mass spectrum: m/z= 145.1 (M+1).

and hexahydro-5-imino-2-methyl-1,4-thiazepine hydrochloride (see Example 7).

EXAMPLE 7

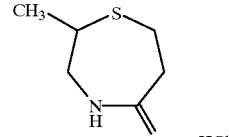

Hexahydro-5-imino-2-methyl-1,4-thiazepine Hydrochloride

Hexahydro-5-imino-2-methyl-1,4-thiazepine hydrochloride was prepared according to the procedures described in Example 6.

$^1$H NMR (500 MHz, CD$_3$OD): δ 3.80 (ABq, 2H), 3.30 (m, 1H), 3.12 (m, 2H), 2.80 (ABq, 2H), 1.39 (d, 3H, J=7 Hz). $^{13}$C NMR (125 MHz, CD$_3$OD) δ 46.62, 42.25, 32.51, 28.01, 20.26. Mass spectrum: m/z=145.2 (M+1).

EXAMPLE 8

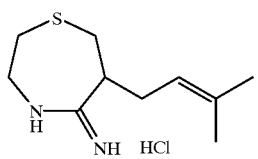

Hexahydro-5-imino-6-(3-methyl-2-n-butenyl)-1,4-thiazepine Hydrochloride

Employing the procedures described in Example 4, but substituting 1-bromo-3-methyl-2-n-butene for 1-iodopropane in step B, the 6-positional isomer was separated from the 3-positional isomer (see Example 9) as its respective thioamide by flash column chromatography. Subsequently, reaction with Meerwein's salt and ammonium chloride as described in Example 2, step D gave hexahydro-5-imnino-6-(3-methyl-2-n-butenyl)-1,4-thiazepine hydrochloride.

$^1$H NMR (500 MHz, CD$_3$OD): δ 5.10 (m, 1H), 4.15, (m, 1H), 3.79 (m, 1H), 1.75 (s, 3H), 1.71 (s, 3H). Mass spectrum: m/z=199.2 (M+1).

EXAMPLE 9

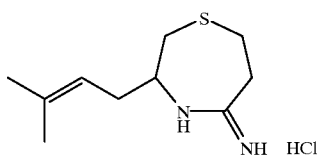

Hexahydro-5-imino-3-(3-methyl-2-n-butenyl)-1,4-thiazepine Hydrochloride

Employing the procedures described in Example 4, but substituting 1-bromo-3-methyl-2-n-butene for 1-iodopropane in step B, the 3-positional isomer was separated from the 6-positional isomer (see Example 8) by flash column chromatography as its respective thioamide. Subsequently, reaction with Meerwein's salt and ammonium chloride as described in Example 2, step D gave hexahydro-5-imino-3-(3-methyl-2-n-butenyl)-1,4-thiazepine hydrochloride.

$^1$H NMR (500 MHz, CD$_3$OD): δ 5.17 (br t, 1H), 3.96 (ABq, 2H), 3.22 (m, 1H), 3.09 (m, 1H), 2.45 (m, 2H), 1.75 (s, 3H), 1.70 (s, 3H). $^{13}$C NMR (125 MHZ, CD$_3$OD) δ 118.04, 59.14, 35.09, 33.38, 32.93, 24.63, 23.36, 16.81. Mass spectrum: m/z=199.2 (M+1).

EXAMPLE 10

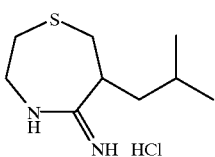

Hexahydro-5-imino-6-(2-methyl-propyl)-1,4-thiazepine Hydrochloride

Employing the procedures described in Example 4, but substituting isobutyl iodide for 1-iodopropane in step B, the 6-positional isomer was separated from the 3-positional isomer (see Example 11) as its respective thioamide by flash column chromatography. Subsequently, reaction with Meerwein's salt and ammonium chloride as described in Example 2, step D gave hexahydro-5-imino-6-(2-methyl-propyl)-1,4-thiazepine hydrochloride.

$^1$H NMR (500 MHz, CD$_3$OD): δ 3.77 (t, 2H), 3.25 (m, 1H), 2.95 (d of d, 1H), 2.83 (m, 1H), 2.73 (m, 2H), 1.87 (m, 1H), 1.70 (m, 2H), 1.01 (d, 3H), 0.99 (d, 3H). Mass spectrum: m/z=187.2.

EXAMPLE 11

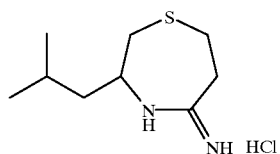

Hexahydro-5-imino-3-(2-methyl-propyl)-1,4-thiazepine Hydrochloride

Employing the procedures described in Example 4, but substituting isobutyl iodide for 1-iodopropane in step B, the 3-positional isomer was separated from the 6-positional isomer (see Example 10) as its respective thioamide by flash column chromatography. Subsequently, reaction with Meerwein's salt and ammonium chloride as described in Example 2, step D gave hexahydro-5-imino-3-(2-methyl-propyl)-1,4-thiazepine hydrochloride.

$^1$H NMR (500 MHz, CD$_3$OD): δ 3.95 (m, 1H), 3.25 (m, 1H), 3.10 (m, 1H), 2.87 (m, 1H), 2.80 (m, 1H), 2.73 (d, 1H), 2.65 (d of d, 1H), 1.76 (m, 1H), 1.69 (m, 1H), 1.5 (m, 1H), 0.98 (t, 6H) Mass spectrum: m/z=187.2.

EXAMPLE 12

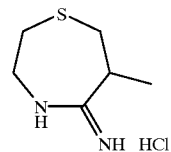

Hexahydro-5-imino-6-methyl-1,4-thiazepine Hydrochloride

Employing the procedures described in Example 4, but substituting methyl iodide for 1-iodopropane in step B, the 6-positional isomer was separated from the 3-positional isomer (see Example 13) as its respective thioamide by flash column chromatography. Subsequently, reaction with Meerwein's salt and ammonium chloride as described in Example 2, step D gave hexahydro-5-imino-6-methyl-1,4-thiazepine hydrochloride.

$^1$H NMR (500 MHz, CD$_3$OD): δ 3.78 (t, 2H), 3.4 (m, 1H), 2.82 (m, 2H), 2.72 (m, 2H), 1.42 (d, 3H) Mass spectrum: m/z=145.0

EXAMPLE 13

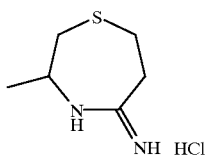

Hexahydro-5-imino-3-methyl-1,4-thiazepine Hydrochloride

Employing the procedures described in Example 4, but substituting methyl iodide for 1-iodopropane in step B, the 3-positional isomer was separated from the 6-positional isomer (see Example 13) as its respective thioamide by flash column chromatography. Subsequently, reaction with Meerwein's salt and ammonium chloride as described in Example 2, step D gave hexahydro-5-imino-3-methyl-1,4-thiazepine hydrochloride.

$^1$H NMR (500 MHz, CD$_3$OD): δ 4.07 (m, 1H), 3.19 (m, 1H), 3.04 (m, 1H), 2.80 (m, 2H), 2.69 (m, 2H), 11.39 (d, 3H) Mass spectrum: mn/z=145.1.

EXAMPLE 14

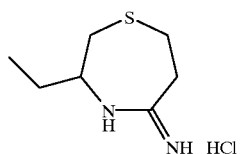

Hexahydro-5-imino-3-ethyl-1,4-thiazepine Hydrochloride

Employing the procedures described in Example 4, but substituting ethyl iodide for 1-iodopropane in step B, the 3-positional isomer was separated from the 6-positional isomer as its respective thioamide by flash column chromatography. Subsequently, reaction with Meerwein's salt and ammonium chloride as described in Example 2, step D gave hexahydro-5-imino-3-ethyl-1,4-thiazepine hydrochloride.

$^1$H NMR (500 MHz, CD$_3$OD): δ 3.87 (m, 1H), 3.23 (m, 1H), 3.06 (m, 1H), 2.80 (m, 2H), 2.64 (d of d, 2H), 1.75 (m, 2H), 1.04 (t, 3H). Mass spectrum: m/z 159.1.

EXAMPLE 15

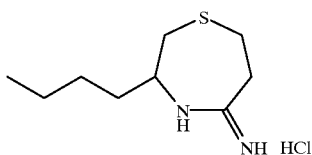

Hexahydro-5-imino-3-butyl-1,4-thiazepine. Hydrochloride

Employing the procedures described in Example 4, but substituting butyl iodide for 1-iodopropane in step B, the 3-positional isomer was separated from the 6-positional isomer as its respective thioamide by flash column chromatography. Subsequently, reaction with Meerwein's salt and ammonium chloride as described in Example 2, step D gave hexahydro-5-imino-3-butyl-1,4-thiazepine, hydrochloride.

$^1$H NMR (500 MHz, CD$_3$OD): δ 3.90 (m, 1H), 3.23 (m, 1H), 3.02 (m, 1H), 2.80 (m, 2H), 2.63 (d of d, 1H), 1.70 (m, 3H), 1.40 (m, 4H), 0.94 (t, 3H). Mass spectrum: m/z=187.2.

EXAMPLE 16

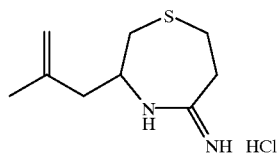

Hexahydro-5-imino-3-(2-methyl-3-propenyl)-1,4-thiazepine Hydrochloride.

Employing the procedures described in Example 4, but substituting 3-bromo-2-methylpropene for 1-iodopropane in step B, the 3-positional isomer was separated from the 6-positional isomer as its respective thioamide by flash column chromatography. Subsequently, reaction with Meerwein's salt and ammonium chloride as described in Example 2, step D gave hexahydro-5-imino-3-(2-methyl-3-propenyl)-1,4-thiazepine hydrochloride.

$^1$H NMR (500 MHz, CD$_3$OD): δ 4.85 (s, 1H), 4.75 (s, 1H), 4.13 (m, 1H), 3.28 (m, 1H), 3.12 (m, 1H), 2.88 (m, 1H), 2.82 (m, 1H), 2.78 (d, 1H), 2.66 (d of d, 1H), 2.45 (m, 2H), 1.78 (s, 3H). Mass spectrum: m/z=185.1.

EXAMPLE 17

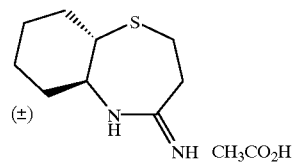

(±)-trans-Decahydro-4-imino-benzo[b]-1,4-thiazepine Acetic Acid Salt

Step A: (±)-trans-2-(tert-Butoxycarbonyl)-cyclohexanol

To a vigorously stirring solution of trans-2-aminocyclohexanol hydrochloride (5.5 g, 36 mmol) in 100 mL methylene chloride and saturated sodium bicarbonate solution (1:1) at 0° C. was added di-tert-butylcarbonate (13.09 g, 60 mmol). The resulting heterogeneous mixture was warmed to the room temperature and stirred overnight. The methylene chloride layer was washed with brine, dried and evaporated. The solid obtained was triturated with hexane and filtered to give 5.86 g (96%) of (±)-trans-2-N-(tert-butoxycarbonyl)-cyclohexanol.

$^1$H NMR (500 MHz, CDCl$_3$): δ 4.61(brs, 1H), 3.27 (m, 1H), 2.73 (brs, 1H), 2.02–1.69 (m, 4H), 1,45 (s, 9H), 1.42–1.09(m, 4H). $^{13}$C NMR (125 MHz, CDCl$_3$): δ 75.42, 56.62, 34.22, 31.84, 28.43, 27.48, 24.78, 24.11.

Step B: (±)-7-(tert-Butoxycarbonyl)-7-aza-bicyclo-[4.1.01]-cycloheptane

To a stirring mixture of (±)-trans-2—N-(tert-butoxycarbonyl)-cyclohexanol (4.08 g, 20 mmol) and triphenylphosphine (10.49 g, 40 mmol) in 50 mL of tetrahydrofuran at 0° C. was slowly added diisopropyl azodicarboxylate (8.08 g, 40 mmol). The reaction mixture was warmed to the room temperature and stirred until the TLC indicated the disappearence of the starting alcohol (μappro. 2–4 hrs). The tetrahydrofuran was evaporated in vacuo and the crude product was passed through a silica gel column and eluted with hexane/methylene chloride (1:1) to give 3.18 g (85%) of the desired (±)-7-(tert-butoxycarbonyl)-7-aza-bicyclo-[4.1.0]-cycloheptane as an oil.

$^1$H NMR (500 MHz, CDCl$_3$): δ 2.55 (m, 2H), 1.93–1.75 (m, 4H), 1.45 (s, 9H), 1.44–1.21(m, 4H). $^{13}$C NMR (125 MHz, CDCl$_3$): δ 80.62, 36.96, 28.04, 23.80, 19.93.

Step C: (±)-trans-2-amino-1-[2-(carboxy)ethylthio]-cyclohexane Hydrochloride (±)-7-(tert-Butoxycarbonyl)-7-aza-bicyclo-[4.1.0]- cycloheptane (0.5 g, 2.68 mmol) was dissolved in 2 mL dimethylformamide and βmercaptopropionic acid (0.318 g, 3 mmol). After the addition of cesium carbonate (1.95 g, 6 mmol), the mixture was stirred at 60° C. until the TLC indicated the full consumption of starting material (appro. 4 hrs). The reaction mixture was diluted with water, the pH was adjusted to 4 (with 2.4 M HCl) and finally extracted with methylene chloride. The solvent layer was washed with brine, dried and evaporated to give the crude (±)-trans-2-(tert-butocycarbonylamino)-1-[2-(carboxy)ethylthio]-cyclohexane, which was not purified but taken to the next stage. The crude from the above was dissolved in 10 ml ethyl acetate saturated with hydrogen chloride and stir at room temperature. The white precipitate that resulted was filtered and dried under vacuo yielding 0.636 g of (±)-trans-2-amino-1-[2-(carboxy)ethylthio]-cyclohexane.

$^1$H NMR (500 MHz, D$_2$O): δ 3.20 (m, 1H), 2.81–2.65 (m, 3H), 2.24 (m, 2H), 1.79–1.2 (m, 8H).

Step D: (±)-trans-Decahydro-4-oxo-benzo[b]-1,4-thiazepine

To (±)-trans-2-amino-1-[2-(carboxy)ethylthio]-cyclohexane hydrochloride (0.240 g, 1 mmol) dissolved in 2 mL of dimethylformaamide at 0° C. was successively added 1-ethyl-3-( 3-dimethylaminopropyl) carbodiimide (0.356 g, 1.2 mmol), 1-hydroxy-7-azabenzotriazole (0.164 g, 1.2 mmol) and then finally N-methylmorpholine (0.252 g, 2.5 mmol). After stirring for an additional 5 mins., the reaction mixture was warmed to room temperature and stirred overnight at the same temperature. The following day the reaction mixture was diluted with water and extracted with methylene chloride.

The solvent layer was washed with brine, dried and evaporated to give the crude which was purified by silica column and eluted with hexane/ethylacetate (7:3 +5% methanol) to give 0.102 g (55%) of (±)-trans-decahydro-4-oxo-benzo[b]-1,4-thiazepane as white solid.

$^1$H NMR (500 MHz, CDCl$_3$): δ 5.66 (s, 1H), 3.46 (m, 1H), 2.98–2.64 (m, 5H), 2.05–1.74 (m, 4H), 1.39–1.21 (m, 4H). $^{13}$C NMR (125 MHz, CDCl$_3$): δ 175.94, 58.07, 46.78, 40.50, 33.77, 31.70, 25.32, 24,67, 24.52.

Step E: (±)-trans-Decahydro-4-thioxo-benzo[b]-1,4-thiazepine

To a solution of (±)-trans-decahydro-4-oxo-benzo[b]-1,4-thiazepane (0.100 g, 0.54 mmol) in 5 mL of dry toluene was added Lawesson's reagent [2,4-bis(4-methoxyphenyl)-1,3-dithia-2,4-diphosphetane-2,4-disulfide] (0. 328 g, 0.81 mmol) and the mixture was stirred at 90° C. for 30 mins. Evaporation of the solvent in vacuo followed by purification by flash column chromatography on silica gel eluted with methylene chloride: ethyl acetate (19: 1) gave 0. 083 g (77%) of (±)-trans-decahydro-4-thioxo-benzo [b] -1,4-thiazepine.

$^1$H NMR (500 MHz, CDCl$_3$): δ 7.70 (brs, 1H), 3.72 (m, 1H), 3.65 (m, 1H), 3.23 (m, 1H), 2.96 (m, 1H), 2.77–2.65 (m, 2H), 2.14–1.25 (m, 8H). $^{13}$C NMR (125 MHZ, CDCl$_3$): δ 63.26, 48.42, 44.43,33.73,31.41, 26.45, 25.06, 24.31.

Step F: (±)-trans-Decahydro-4-imino-benzo[b]-1,4-thiazepine Acetic Acid Salt.

To a solution of (±)-trans-decahydro-4-thioxo-benzo[b]-1,4-thiazepane (25 mg, 0.12 mmol) in 2 mL of dry methylene chloride at room temperature was added trimethyloxonium tetrafluoroborate (Meerwein's salt) (24 mg, 0.16 mmol). The resulting mixture was stirred at room temperature overnight. The reaction mixture was quenched with saturated solution of sodium bicarbonate solution and stir for 5 mins. The methylene chloride layer was washed with water, saturated sodium chloride solution and dried over anhydrous magnesium sulfate. The solvent was removed in vacuo to give the crude imino-ether which was subsequently treated with ammonium chloride (14 mg) in 4 mL of ethanol and heated at 80° C. for 4 h. Evaporation of ethanol followed by purification by column chromatography and elution with acetonitrile:

water:acetic acid (90:5:5) gave 21.8 mg (±)-trans-decahydro-4-imino-benzo[b]-1,4-thiazepine acetic acid salt.

$^1$H NMR (500 MHz, D$_2$O): δ 3.68 (m, 1H), 3.64 (m, 1H), 3.26–2.83 (m, 4H), 2.06–1.23 (m, 8H). $^{13}$C NMR (125 MHZ, CDCl$_3$ ): δ 58.72, 45.32, 33.96, 31.85, 31,76, 20 25.00, 23.95, 21.47. Mass spectrum: m/z=185.1 (M$^+$).

EXAMPLE 18

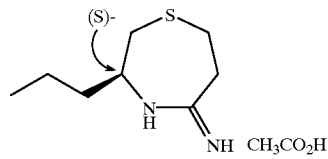

Hexahydro-5-imino-3(S)-propyl-1,4-thiazepine, Acetic Acid Salt

Step A: Tetrahydro-3(S)-propyl-(2H)-1,4-thiazepine-5-thione

The title compound was prepared employing the procedure in Example 17, Steps A to E and starting from L-norvalinol instead of (±)-trans-2-aminocyclohexanol.

Step B: Hexahydro-5-imino-3(S)-propyl-1,4-thiazepine Acetic Acid Salt

To a solution of tetrahydro-3(S)-propyl-(2H)-1,4-thiazepine-5-thione (42 mg, 0.22 mmol) in 5 mL tetrahydrofuran and saturated with ammonia gas at 60° C. was added mercuric chloride (73.3 mg, 0.27 mmol). The stream of ammonia gas was bubbled for another 10 mins. at the same temperature. After stirring for 2 h, the reaction mixture was filtered and the filtrate was evaporated. The crude compound was then purified by column chromatography and eluted with acetonitrile:water:acetic acid (90:5:5) giving 31.5 mg of hexahydro-5-imino-3(S)-propyl-1,4-thiazepine acetic acid salt.

$^1$H NMR (500 MHz, CD$_3$OD): δ 3.93 (m, 1H), 3.30–2.61 (m, 6H), 1.72–1.40 (m, 4H), 0.97 (t, 3H, J=7.3 Hz). $^{13}$C NMR (125 MHZ, CD$_3$OD): δ 58.58, 36.42, 34.95, 34.09, 23.33, 18.87, 12.61. Mass spectrum: m/z=173.1 (M+1).

EXAMPLE 19

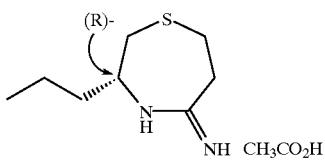

Hexahydro-5-imino-3(R)-propyl-1,4-thiazepine Acetic Acid Salt

Step A: Tetrahydro-3(R)-propyl-(2H)-1,4-thiazepine-5-thione

The title compound was prepared employing the procedure in Example 17, Steps A–E and starting from D-norvalinol instead of (±)-trans-2-aminocyclohexanol.

Step B: Hexahydro-5-imino-3(R)-propyl-1,4-thiazepine Acetic Salt

Employing the procedure 19, step B, tetrahydro-3(R)-propyl-(2H)-1,4-thiazepine-5-thione (40 mg, 0.21 mmol) was converted to 37.4 mg of hexahydro-5-imino-3(R)-propyl-1,4-thiazepine acetic acid salt.

$^1$H NMR (500 MHz, CD$_3$OD): d 3.93 (m, 1H), 3.29–3.02 (m, 2H), 2.87–2.61 (m, 4H), 1.73–1.41 (m, 4H), 0.97 (t, 3H, J=7.3 Hz). $^{13}$C NMR (125 MHZ, CD$_3$OD): d 58.60, 36.43, 34.96, 34.10, 23.35, 18.87, 12.63. Mass spectrum: m/z= 173.1 (M+1).

EXAMPLE 20

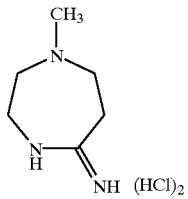

Hexahydro-5-imino-1-methyl-1H-1,4-diazepine Hydrochloride.

Employing the method of Foloppe et al. (M.P. Foloppe, S. Rault, and M. Robba, *Tetrahedron Lett.* 1992, 33, 2803–2804), a solution of hexahydro-1-methyl-(5H)-1,4-diazepin-5-thione (R. Guryn, *Polish J. Chem.* 1987, 61, 259–262) (100 mg, 0.694 mmol) in tetrahydrofuran (5.0 mL) was warmed in a 55° C. oil bath as ammonia was bubbled into the solution. Mercuric chloride (207 mg, 0.764 mmol) was added in one portion, and the mixture quickly became black. After 20 min, the introduction of ammonia was discontinued and the mixture was stirred at room temperature for 1 h. The mixture was then centrifuged and the supernatant was decanted. The pellet was resuspended in tetrahydrofuran (3 mL), the mixture was centrifuged, and the supernatant was decanted. This was repeated with 2×3 mL of tetrahydrofuran and then 3×3 mL of methanol. The methanol extracts were combined, filtered through a 0.45 micron membrane, and evaporated to give 131 mg of white solid. Based on the combustion analysis for carbon, this material contained 92 mg (82% yield) of hexahydro-5-imino-1-methyl-(1H)-1,4-diazepine hydrochloride salt.

$^1$H NMR (400 MHz, CD$_3$OD): δ 3.56–3.52 (m, 2H), 2.88 (dd, 2H, J=6 Hz, 3 Hz), 2.79–2.71 (m, 2H), 2.71–2.63 (m, 2H), 2.43 (s, 3H). Mass spectrum: m/z=128 (M–HCl +1).

Anal. calc'd. for C$_6$H$_{14}$N$_3$Cl.1.23 NH$_4$Cl: C, 31.1; H, 8.40; N, 25.5; Cl, 34.1. Found: C, 31.08; H, 8.16; N, 23.41; Cl, 34.06.

What is claimed is:

1. A compound selected from the group consisting of:
   (a) hexahydro-5-imino-3-propyl-1,4-thiazepine hydrochloride,
   (b) hexahydro-5-imino-6-propyl-1,4-thiazepine hydrochloride,
   (c) hexahydro-5-imino-7-methyl-1,4-thiazepine hydrochloride,
   (d) hexahydro-5-imino-2-methyl-1,4-thiazepine hydrochloride,
   (e) hexahydro-5-imino-6-(3-methyl-2-n-butenyl)-1,4-thiazepine hydrochloride,
   (f) hexahydro-5-imino-3-(3-methyl-2-n-butenyl)-1,4-thiazepine hydrochloride,
   (g) hexahydro-5-imino-6-(2-methyl-propyl)-1,4-thiazepine hydrochloride,
   (h) hexahydro-5-imino-3-(2-methyl-propyl)-1,4-thiazepine hydrochloride,
   (i) hexahydro-5-imino-6-methyl-1,4-thiazepine hydrochloride,
   (j) hexahydro-5-imino-3-methyl-1,4-thiazepine hydrochloride,
   (k) hexahydro-5-imino-3-ethyl-1,4-thiazepine hydrochloride,
   (l) hexahydro-5-imino-3-butyl-1,4-thiazepine hydrochloride,
   (m) hexahydro-5-imino-3-(2-methyl-3-propenyl)-1,4-thiazepine hydrochloride,
   (n) (±)-trans-decahydro-4-imino-benzo[b]-1,4-thiazepine acetic acid salt,
   (o) hexahydro-5-imino-3(S)-propyl-1,4-thiazepine acetic acid salt,
   (p) hexahydro-5-imino-3(R)-propyl-1,4-thiazepine acetic acid salt,
   and pharmaceutically acceptable salts thereof.

2. A compound according to claim 1 which is hexahydro-5-imino-3-propyl-1,4-thiazepine hydrochloride.

3. A pharmaceutical composition comprising a pharmaceutical carrier and a non-toxic effective amount of the compound of Formula I

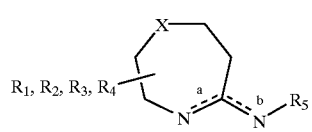

or a pharmaceutically acceptable salt thereof wherein:
   side a or side b has a double bond, with the proviso that when side b has a double bond a hydrogen atom is bonded to the nitrogen atom in the ring and when side a has a double bond a hydrogen atom is bonded to the nitrogen atom not in the ring,
   X is S(O)$_m$,
   m is 0, 1 or 2;
   R$_1$, R$_2$, R$_3$ and R$_4$ are each independently selected from the group consisting of:
   (a) hydrogen,
   (b) C$_{1-12}$alkoxy, (c) $C_{1-12}$alkyl-S(O)$_k$ wherein k is 0, 1 or 2,
(d) mono $C_{1-12}$alkylamino,
(e) (di-$C_{1-12}$alkyl)amino,
(f) $C_{1-12}$alkylcarbonyl,
(g) $C_{1-12}$alkyl,
(h) $C_{2-12}$alkenyl,
(i) $C_{2-12}$alkynyl,
(j) $C_{5-10}$cycloalkyl,
(k) hetero $C_{5-10}$ocycloalkyl, wherein the hetero $C_{5-10}$-cycloalkyl contains 1 or 2 heteroatoms selected from S, O and N,
(l) aryl selected from phenyl and naphthyl,
(m) heteroaryl, wherein heteroaryl is selected from the group consisting of:
  (1) benzimidazolyl,
  (2) benzofuranyl,
  (3) benzooxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) pyrazinyl,
  (12) pyrazolyl,
  (13) pyridyl,
  (14) pyrimidyl,
  (15) pyrrolyl,
  (17) isoquinolyl,
  (18) tetrazolyl,
  (19) thiadiazolyl,
  (20) thiazolyl,
  (21) thienyl and
  (22) triazolyl,
(n) $C_{1-12}$alkyl-C(O)NH,
(o) $C_{1-12}$alkoxy-C(O)NH,
(p) $C_{1-12}$alkylamino-C(O)NH,
(q) $C_{1-12}$alkyl-S(O)$_2$NH,
(r) $C_{1-12}$alkylamino-C(O),
(s) $C_{1-12}$alkylamino-S(O)$_2$,
(t) aryl-C(O)NH where aryl is selected from phenyl, naphthyl, pyridyl, thienyl, thiazolyl, oxazolyl, imidazolyl and triazolyl,
(u) aryloxy-C(O)NH where aryl is selected from phenyl, naphthyl and pyridyl,
(v) phenylamnino-C(O)NH,
(w) aryl-S(O)$_2$NH where aryl is selected from phenyl and naphthyl,
(x) aryl-C(O) where aryl is selected from phenyl, naphthyl, pyridyl, thienyl, thiazolyl, oxazolyl, imidazolyl and triazolyl,
(y) phenylamino-S(O)$_2$,
(z) hydroxy,
(aa) amino,
(ab) oxo and
(ac) C(O)OR$_7$ wherein R$_7$ is selected from hydrogen, phenyl, benzyl, cyclohexyl and $C_{1-6}$alkyl,
each of (b) to (y) being optionally mono or di-substituted, the substituents being independently selected from:
  (1) hydroxy,
  (2) carboxy,
  (3) —NR$_7$R$_8$, where R$_8$ is selected from hydrogen, phenyl, benzyl, cyclohexyl and $C_{1-6}$alkyl,
  (4) —NR$_7$C(O)R$_8$
  (5) —NR$_7$C(O)NHR$_8$,
  (6) —NR$_7$C(O)OR$_9$, where R$_9$ is selected from phenyl, benzyl, cyclohexyl and $C_{1-6}$alkyl,
  (7) —NR$_7$S(O)$_2$R$_9$,
  (8) —OR$_7$,
  (9) —C(O)OR$_9$,
  (10) —C(O)NR$_7$R$_8$,
  (11) —C(O)R$_7$,
  (12) —S(O)$_k$R$_7$,
  (13) —S(O)$_2$NR$_7$R$_8$,
  (14) halo selected from F, Cl, Br and I,
  (15) -trifluoromethyl,
  (16) —C(=NR$_7$)—NHR$_8$,
  (17) hetero $C_{5-10}$ocycloalkyl, wherein the hetero $C_{5-10}$-cycloalkyl optionally contains 1 or 2 heteroatoms selected from S, O and N,
  (18) aryl, selected from phenyl and naphthyl, and
  (19) heteroaryl, wherein heteroaryl is selected from the group consisting of:
    (a) imidazolyl,
    (b) isooxazolyl,
    (c) isothiazolyl,
    (d) oxadiazolyl,
    (e) oxazolyl,
    (f) pyridyl,
    (g) tetrazolyl,
    (h) thiazolyl,
    (i) thienyl and
    (j) triazolyl,
or when two members of the group R$_1$, R$_2$, R$_3$ and R$_4$ reside on the same carbon atom of Formula I, or two of the group R$_1$, R$_2$, R$_3$ and R$_4$ reside on adjacent atoms of Formula I, said two members along with the optional substituents thereon may optionally be joined, such that together with the carbon atom to which they are attached there is formed a saturated or unsaturated monocyclic ring of 5, 6 or 7 atoms, said monocyclic ring optionally containing up to three hetero atoms selected from N, O and S,
R$_5$ is selected from the group consisting of:
  (a) hydrogen,
  (b) linear and branched $C_{1-12}$alkyl, optionally mono or di-substituted, the substituents being independently selected from:
    (1) hydroxy,
    (2) carboxy,
    (3) —NR$_7$R$_8$,
    (4) —OR$_7$,
    (5) —C(O)OR$_7$,
    (6) —S(O)$_k$R$_7$,
    (7) halo selected from F, Cl, Br and I,
    (8) trifluoromethyl and
    (9) phenyl, optionally mono or di-substituted with a substituent selected from hydroxy, halo, $C_{1-4}$alkyl, and $C_{1-4}$alkoxy,
  (c) —C(O)NR$_{10}$R$_{11}$, where R$_{10}$ and R$_{11}$ are each independently hydrogen, phenyl, cyclohexyl, —S(O)$_2$NR$_7$R$_8$ and optionally substituted $C_{1-6}$alkyl, wherein said substituent is selected from
    (1) —NR$_{12}$R$_{13}$, wherein R$_{12}$ and R$_{13}$ are each independently selected from H, $C_{1-6}$alkyl, phenyl and benzyl,
    (2) -OR$_{12}$,
    (3) —C(O)OR$_{12}$,
    (4) —S(O)$_k$R$_{12}$, where m is 0, 1 or 2,
    (5) halo selected from F, Cl, Br and I,
    (6) optionally substituted aryl wherein aryl and aryl substituents are as defined above, (7) optionally substituted heteroaryl wherein heteroaryl and heteroaryl substituents are as defined above,
(8) optionally substituted $C_{5-10}$cycloalkyl wherein cycloalkyl and cycloalkyl substituents are as defined above, and
(9) hetero $C_{5-10}$-cycloalkyl, wherein the hetero $C_{5-10}$-cycloalkyl optionally contains 1 or 2 heteroatoms selected from S, O and N,
(d) —C(O)$R_{11}$,
(e) —C(O)O$R_{11}$,
(f) aryl, selected from phenyl and naphthyl, and
(g) cyclohexyl.

4. The pharmaceutical composition according to claim 3, wherein:

$R_1$ and $R_2$ are each independently selected from the group consist of
(a) hydrogen,
(b) $C_{1-2}$alkoxy,
(c) $C_{1-12}$alkyl-S(O)$_k$ wherein k is 0, 1 or 2,
(d) mono $C_{1-12}$alkylamino,
(e) (di-$C_{1-12}$alkyl)amino,
(f) $C_{1-12}$alkylcarbonyl,
(g) $C_{1-12}$alkyl,
(h) $C_{2-12}$alkenyl,
(i) $C_{2-12}$alkynyl,
(j) $C_{5-10}$-cycloalkyl,
(k) hetero $C_{5-10}$-cycloalkyl, wherein the hetero $C_{5-10}$cycloalkyl contains 1 or 2 heteroatoms selected from S, O and N,
(l) aryl, selected from phenyl or naphthyl,
(m) heteroaryl, wherein heteroaryl is selected from the group consisting of:
(1) benzimidazolyl,
(2) benzofuranyl,
(3) benzooxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(17) isoquinolyl,
(18) tetrazolyl,
(19) thiadiazolyl,
(20) thiazolyl,
(21) thienyl, and
(22) triazolyl,
(n) $C_{1-12}$alkyl-C(O)NH,
(o) $C_{1-12}$alkoxy-C(O)NH,
(p) $C_{1-12}$alkylamino-C(O)NH,
(q) $C_{1-12}$alkyl-S(O)$_2$NH,
(r) $C_{1-12}$alkylamino-C(O),
(s) $C_{1-12}$alkylamino-S(O)$_2$,
(t) aryl-C(O)NH where aryl is selected from phenyl, naphthyl, pyridyl, thienyl, thiazolyl, oxazolyl, imidazolyl, and triazolyl,
(u) aryloxy-C(O)NH where aryl is selected from phenyl, naphthyl, and pyridyl,
(v) phenylamino-C(O)NH,
(w) aryl-S(O)$_2$NH where aryl is selected from phenyl and naphthyl,
(x) aryl-C(O) where aryl is selected from phenyl, naphthyl, pyridyl, thienyl, thiazolyl, oxazolyl, imidazolyl, and triazolyl,
(y) phenylamino-S(O)$_2$,
(z) hydroxy,
(aa) amino,
(ab) oxo,
(ac) C(O)O$R_7$, $R_7$ is selected from hydrogen, phenyl, benzyl, cyclohexyl and $C_{1-6}$alkyl, each of (b) to (y) being optionally mono or di-substituted, the substituents being independently selected from
(1) hydroxy,
(2) carboxy,
(3) —NR$_7$R$_8$, where $R_8$ is selected from hydrogen, phenyl, benzyl, cyclohexyl and $C_{1-6}$alkyl,
(4) —NR$_7$C(O)R$_8$
(6) —NR$_7$C(O)NHR$_8$,
(5) —NR$_7$C(O)OR$_9$, where $R_9$ is selected from phenyl, benzyl, cyclohexyl and $C_{1-6}$alkyl
(7) —NR$_7$S(O)$_2$R$_9$,
(8) —OR$_7$,
(9) —C(O)OR$_9$,
(10) —C(O)NR$_7$R$_8$,
(11) —C(O)R$_7$,
(12) —S(O)$_k$R$_7$,
(13) —S(O)$_2$NR$_7$R$_8$,
(14) halo selected from F, Cl, Br and I,
(15) -trifluoromethyl,
(16) —C(=NR$_7$)-NHR$_8$,
(17) hetero $C_{5-10}$cycloalkyl, wherein the hetero $C_{5-10}$cycloalkyl contains 1 or 2 heteroatoms selected from S, O and N,
(18) aryl, selected from phenyl or naphthyl,
(19) heteroaryl, wherein heteroaryl is selected from the group consisting of:
(a) imidazolyl,
(b) isooxazolyl,
(c) isothiazolyl,
(d) oxadiazolyl,
(e) oxazolyl,
(f) pyridyl,
(g) tetrazolyl,
(h) thiazolyl,
(i) thienyl, and
(j) triazolyl, $R_3$ and $R_4$ reside on the same carbon atom of Formula I, or reside on adjacent atoms of Formula I, and $R_3$ and $R_4$ are joined such that together with the carbon atom to which they are attached there is formed a saturated or unsaturated monocyclic ring of 5, 6 or 7 atoms, said monocyclic ring optionally containing up to three hetero atoms selected from N, O or S, and $R_5$ is selected from the group consisting of:
(a) hydrogen,
(b) linear and branched $C_{1-12}$alkyl, optionally mono or di-substituted, the substituents being independently selected from
(1) hydroxy,
(2) carboxy,
(3) —NR$_7$R$_8$,
(4) —OR$_7$,
(5) —C(O)OR$_7$,
(6) —S(O)$_k$R$_7$,
(7) halo selected from F, Cl, Br and I,
(8) trifluoromethyl,
(9) phenyl, optionally mono or di-substituted with hydroxy, halo, $C_{1-4}$alkyl, or $C_{1-4}$alkoxy, (c) —C(O)NR$_{10}$R$_{11}$, where R$_{10}$ and R$_{11}$ are each independently hydrogen, phenyl, cyclohexyl, —S(O)$_2$NR$_7$R$_8$ or C$_{1-6}$alkyl, said C$_{1-6}$alkyl optionally substituted by
  (1) —NR$_{12}$R$_{13}$, wherein R$_{12}$ and R$_{13}$ are each independently H, C$_{1-6}$alkyl, phenyl or benzyl,
  (2) —OR$_{12}$,
  (3) —C(O)OR$_{12}$,
  (4) —S(O)$_k$R$_{12}$, where m is 0, 1 or 2,
  (5) halo selected from F, Cl, Br and I,
  (6) optionally substituted aryl wherein aryl and aryl substituents are as defined above,
  (7) optionally substituted heteroaryl wherein heteroaryl and heteroaryl substituents are as defined above,
  (8) optionally substituted C$_{5-10}$-cycloalkyl wherein cycloalkyl and cycloalkyl substituents are as defined above,
  (9) hetero C$_{5-10}$cycloalkyl, wherein the hetero C$_{5-10}$ocycloalkyl contains 1 or 2 heteroatoms selected from S, O and N,
(d) —C(O)R$_{11}$,
(e) —C(O)OR$_{11}$,
(f) aryl, selected from phenyl or naphthyl,
(g) cyclohexyl.

5. A pharmaceutical composition comprising a pharmaceutical carrier and a non-toxic effective amount of the compound of Formula I

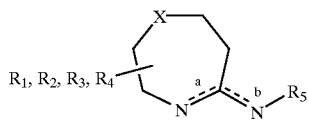

I or a pharmaceutically acceptable salt thereof wherein: side a or side b has a double bond, with the proviso that when side b has a double bond a hydrogen atom is bonded to the nitrogen atom in the ring and when side a has a double bond a hydrogen atom is bonded to the nitrogen atom not in the ring, X is S(O)$_m$,
m is 0, 1 or 2;
R$_1$ and R$_2$ are each independently selected from the group consisting of:
  (a) hydrogen,
  (b) hydroxy,
  (c) amino,
  (d) cyano,
  (e) fluoro, chloro, bromo, and iodo,
  (f) trifluoromethyl,
  (g) C$_{1-6}$alkyl,
  (h) C$_{1-6}$alkoxy,
  (i) C$_{1-6}$alkylthio,
  (j) C$_{1-6}$alkylcarbonyl,
  (k) mono- and di-C$_{1-6}$alkylamino,
  (l) aryl, where aryl is phenyl and naphthyl,
  (m) aryloxy, where aryl is phenyl and naphthyl,
  (n) cycloalkyl, wherein the cycloalkyl is a 5-, 6-, or 7-membered monocyclic ring, and
  (o) heteroaryl, wherein heteroaryl is selected from the group consisting of:
    (1) pyridyl,
    (2) furanyl,
    (3) thienyl,
    (4) pyrazinyl,
    (5) pyrimidyl,
    (6) thiazolyl, and
    (7) triazolyl,
  each of (g) to (o) being optionally mono- or di-substituted, the substituents being independently selected from
    (1) hydroxy,
    (2) C$_{1-4}$alkyl,
    (3) C$_{1-3}$alkoxy,
    (4) amino,
    (5) mono- and di-C$_{1-6}$alkylamino,
    (6) carboxyl,
    (7) C$_{1-3}$alkylthio,
    (8) C$_{1-3}$alkyl-S(O)$_k$—, where k is 1 or 2,
    (9) C$_{1-4}$alkoxycarbonyl,
    (10) halo selected from fluoro, chloro, bromo, and iodo,
    (11) oxo, and
    (12) amidino,
R$_3$ and R$_4$ reside on the same carbon atom of Formula I, or reside on adjacent atoms of Formula I, and R$_3$ and R$_4$ are joined, such that together with the carbon atom to which they are attached there is formed a saturated or unsaturated monocyclic ring of 5 or 6 atoms, said monocyclic ring optionally containing one or 2 hetero atoms selected from N, O or S, and
R$_5$ is selected from the group consisting of:
  (a) hydrogen,
  (b) C$_{1-6}$alkylcarbonyl,
  (c) aroyl, wherein the aroyl group is benzoyl,
  (d) aroylaminocarbonyl, wherein the aroyl group is benzoyl and naphthoyl,
  (e) R$_6$R$_7$N—SO$_2$—NH—C(=O)—, wherein R$_6$ and R$_7$ are independently selected from the group consisting of:
    (1) hydrogen,
    (2) C$_{1-6}$alkyl
    (3) aryl, wherein the aryl group is selected from phenyl, and
    (4) R$_6$ and R$_7$ may be joined together with the nitrogen atom to which they are attached to form a 5-, 6- or 7-membered ring containing 0, 1 or 2 heteroatoms, the heteroatoms being elected from the group of oxygen, sulfur and nitrogen,
  each of (b) to (e) being mono- or di-substituted, the substituents being independently selected from
    (1) hydroxy,
    (2) C$_{1-3}$alkoxy,
    (3) amino,
    (4) mono- and di-C$_{1-6}$alkylamino,
    (5) carboxyl,
    (6) C$_{1-3}$alkylthio,
    (7) C$_{1-3}$alkyl-S(O)$_k$—, where k is 1 or 2,
    (8) C$_{1-4}$alkoxycarbonyl,
    (9) halo selected from fluoro, chloro, bromo, and iodo,
    (10) oxo, and
    (11) amidino.

6. The pharmaceutical composition according to claim 5 wherein:
R$_1$ and R$_2$ are each independently selected from the group consisting of:
  (a) hydrogen,
  (b) hydroxy,
  (c) amino,
  (d) cyano,
  (e) fluoro, chloro or bromo, (f) trifluoromethyl,
(g) $C_{1-4}$alkyl,
(h) $C_{1-4}$alkoxy,
(i) $C_{1-4}$alkylthio, and
(j) mono- and di-$C_{1-4}$alkylamino, $R_3$ and $R_4$ reside on adjacent atoms of Formula I, and $R_3$ and $R_4$ are joined, such that together with the carbon atom to which they are attached there is formed a saturated or unsaturated monocyclic ring of 5 or 6 atoms, said monocyclic ring optionally containing one or 2 hetero atoms selected from N, O or S, and $R_5$ is selected from the group consisting of:
(a) hydrogen,
(b) $R_6R_7N$—$SO_2$—NH—C(=O)—, optionally mono or di-substituted, wherein $R_6$ and $R_7$ are independently selected from the group consisting of
(1) hydrogen,
(2) $C_{1-4}$alkyl, and
(3) aryl, wherein the aryl group is selected from phenyl, and said substituents are independently selected from
(1) hydroxy,
(2) $C_{1-3}$alkoxy,
(3) amino,
(4) mono- and di-$C_{1-6}$alkylamino,
(5) carboxyl,
(6) $C_{1-3}$alkylthio, and
(7) halo selected from fluoro, chloro, and bromo.

7. The pharmaceutical composition according to claim 6 wherein:

$R_1$ and $R_2$ are each independently selected from the group consisting of:
(a) hydrogen,
(b) methyl, ethyl, propyl or butyl,
(c) chloro,
(d) —CN, and
(e) —$CF_3$, $R_3$ and $R_4$ reside on adjacent atoms of Formula I, and $R_3$ and $R_4$ are joined, such that together with the carbon atom to which they are attached there is formed a saturated or unsaturated monocyclic ring of 5 or 6 atoms, said monocyclic ring optionally containing one or 2 hetero atoms selected from N, O or S, and $R_5$ is hydrogen.

8. A pharmaceutical composition comprising a pharmaceutical carrier and a non-toxic effective amount of the compound of Formula I

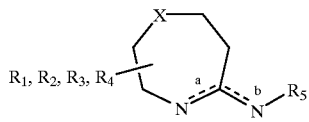

I or a pharmaceutically acceptable salt thereof wherein: side a or side b has a double bond, with the proviso that when side b has a double bond a hydrogen atom is bonded to the nitrogen atom in the ring and when side a has a double bond a hydrogen atom is bonded to the nitrogen atom not in the ring, X is $S(O)_m$,
m is 0, 1 or 2;
$R_1$, $R_2$, $R_3$ and $R_4$ are each independently selected from the group consisting of:

(a) hydrogen,
(b) hydroxy,
(c) amino,
(d) cyano,
(e) fluoro, chloro, bromo, and iodo,
(f) trifluoromethyl,
(g) $C_{1-6}$alkyl,
(h) $C_{1-6}$alkoxy,
(i) $C_{1-6}$alkylthio,
(j) $C_{1-6}$alkylcarbonyl,
(k) mono- and di-$C_{1-6}$alkylamino,
(l) aryl, where aryl is phenyl and naphthyl,
(m) aryloxy, where aryl is phenyl and naphthyl,
(n) cycloalkyl, wherein the cycloalkyl is a 5-, 6-, or 7-membered monocyclic ring, and
(o) heteroaryl, wherein heteroaryl is selected from the group consisting of:
(1) pyridyl,
(2) furanyl,
(3) thienyl,
(4) pyrazinyl,
(5) pyrimidyl,
(6) thiazolyl, and
(7) triazolyl, each of (g) to (o) being optionally mono- or di-substituted, the substituents being independently selected from
(1) hydroxy,
(2) $C_{1-4}$alkyl,
(3) $C_{1-3}$alkoxy,
(4) amino,
(5) mono- and di-$C_{1-6}$alkylamino,
(6) carboxyl,
(7) $C_{1-3}$alkylthio,
(8) $C_{1-3}$alkyl-$S(O)_k$—, where k is 1 or 2,
(9) $C_{1-4}$alkoxycarbonyl,
(10) halo selected from fluoro, chloro, bromo, and iodo,
(11) oxo, and
(12) amidino, and $R_5$ is selected from the group consisting of:
(a) hydrogen,
(b) $C_{1-6}$alkylcarbonyl,
(c) aroyl, wherein the aroyl group is benzoyl,
(d) aroylaminocarbonyl, wherein the aroyl group is benzoyl and naphthoyl,
(e) $R_6R_7N$-$SO_2$—NH—C(=O)—, wherein $R_6$ and $R_7$ are independently selected from the group consisting of
(1) hydrogen,
(2) $C_{1-6}$alkyl,
(3) aryl, wherein the aryl group is selected from phenyl, and
(4) $R_6$ and $R_7$ may be joined together with the nitrogen atom to which they are attached to form a 5-, 6- or 7-membered ring containing 0, 1 or 2 heteroatoms, the heteroatoms being elected from the group of oxygen, sulfur and nitrogen, each of (b) to (e) being mono- or di-substituted, the substituents being independently selected from
(1) hydroxy,
(2) $C_{1-3}$alkoxy,
(3) amino,
(4) mono- and di-$C_{1-6}$alkylamino,
(5) carboxyl,
(6) $C_{1-3}$alkylthio,
(7) $C_{1-3}$alkyl-$S(O)_k$—, where k is 1 or 2, (8) C$_{1-4}$alkoxycarbonyl,
(9) halo selected from fluoro, chloro, bromo, and iodo,
(10) oxo, and
(11) amidino.

9. The pharmaceutical composition according to claim 8 wherein:

R$_1$, R$_2$, R$_3$ and R$_4$ are each independently selected from the group consisting of:
(a) hydrogen,
(b) hydroxy,
(c) amino,
(d) cyano,
(e) fluoro, chloro or bromo,
(f) trifluoromethyl,
(g) C$_{1-4}$alkyl,
(h) C$_{1-4}$alkoxy,
(i) C$_{1-4}$alkylthio, and
(j) mono- and di-C$_{1-4}$alkylamino, and R$_5$ is selected from the group consisting of:
(a) hydrogen,
(b) R$_6$R$_7$N-SO$_2$—NH—C(=O)-, optionally mono or di-substituted, wherein R$_6$ and R$_7$ are independently selected from the group consisting of:
(1) hydrogen,
(2) C$_{1-4}$alkyl, and
(3) aryl, wherein the aryl group is phenyl, and
said substituents are independently selected from the group consisting of:
(1) hydroxy,
(2) C$_{1-3}$alkoxy,
(3) amino,
(4) mono- and di-C$_{1-6}$alkylamino,
(5) carboxyl,
(6) C$_{1-3}$alkylthio, and
(7) halo selected from fluoro, chloro, and bromo.

10. The pharmaceutical composition according to claim 9 wherein:

R$_2$ is hydrogen or methyl;
R$_4$ is hydrogen or methyl;
R$_1$ and R$_3$ are each independently selected from
(a) hydrogen,
(b) methyl, ethyl, propyl or butyl,
(c) chloro,
(d) —CN, and
(e) —CF$_3$; and
R$_5$ is hydrogen.

11. A pharmaceutical composition comprising a pharmaceutical carrier and a non-toxic effective amount of a compound of the following formula

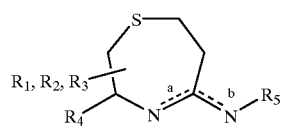

wherein:
side a or side b has a double bond, with the proviso that when side b has a double bond a hydrogen atom is bonded to the nitrogen atom in the ring and when side a has a double bond a hydrogen atom is bonded to the nitrogen atom not in the ring, R$_1$, R$_2$ and R$_3$ are each independently selected from the group consisting of:

(a) hydrogen,
(b) C$_{1-12}$alkoxy,
(c) C$_{1-12}$alkyl-S(O)k wherein k is 0, 1 or 2,
(d) mono C$_{1-12}$alkylamino,
(e) (di-C$_{1-12}$alkyl)amino,
(f) C$_{1-12}$alkylcarbonyl,
(g) C$_{1-12}$alkyl,
(h) C$_{2-12}$alkenyl,
(i) C$_{2-12}$alkynyl,
(j) C$_{5-10}$cycloalkyl,
(k) hetero C$_{5-10}$cycloalkyl, wherein the hetero C$_{5-10}$cycloalkyl contains 1 or 2 heteroatoms selected from S, O and N,
(l) aryl selected from phenyl and naphthyl,
(m) heteroaryl, wherein heteroaryl is selected from the group consisting of:
(1) benzimidazolyl,
(2) benzofuranyl,
(3) benzooxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(17) isoquinolyl,
(18) tetrazolyl,
(19) thiadiazolyl,
(20) thiazolyl,
(21) thienyl and
(22) triazolyl,
(n) C$_{1-12}$alkyl-C(O)NH,
(o) C$_{1-12}$alkoxy-C(O)NH,
(p) C$_{1-12}$alkylamino-C(O)NH,
(q) C$_{1-12}$alkyl-S(O)$_2$NH,
(r) C$_{1-12}$alkylamino-C(O),
(s) C$_{1-12}$alkylamino-S(O)$_2$,
(t) aryl-C(O)NH where aryl is selected from phenyl, naphthyl, pyridyl, thienyl, thiazolyl, oxazolyl, imidazolyl and triazolyl,
(u) aryloxy-C(O)NH where aryl is selected from phenyl, naphthyl and pyridyl,
(v) phenylamino-C(O)NH,
(w) aryl-S(O)$_2$NH where aryl is selected from phenyl and naphthyl,
(x) aryl-C(O) where aryl is selected from phenyl, naphthyl, pyridyl, thienyl, thiazolyl, oxazolyl, imidazolyl and triazolyl,
(y) phenylamino-S(O)$_2$,
(z) hydroxy,
(aa) amino,
(ab) oxo and
(ac) C(O)OR$_7$ wherein R$_7$ is selected from hydrogen, phenyl, benzyl, cyclohexyl and C$_{1-6}$alkyl,
each of (b) to (y) being optionally mono or di-substituted, the substituents being independently selected from:
(1) hydroxy,
(2) carboxy,
(3) —NR$_7$R$_8$, where R$_8$ is selected from hydrogen, phenyl, benzyl, cyclohexyl and C$_{1-6}$alkyl, (4) —NR$_7$C(O)R$_8$,
(5) —NR$_7$C(O)NHR$_8$,
(6) —NR$_7$C(O)OR$_9$, where R$_9$ is selected from phenyl, benzyl, cyclohexyl and C$_{1-6}$alkyl,
(7) —NR$_7$S(O)$_2$R$_9$,
(8) —OR$_7$,
(9) —C(O)OR$_9$,
(10) —C(O)NR$_7$R$_8$,
(11) —C(O)R$_7$,
(12) —S(O)$_k$R$_7$,
(13) —S(O)$_2$NR$_7$R$_8$,
(14) halo selected from F, Cl, Br and I,
(15) -trifluoromethyl,
(16) —C(=NR$_7$)-NHR$_8$,
(17) hetero C$_{5-10}$ocycloalkyl, wherein the hetero C$_{5-10}$cycloalkyl optionally contains 1 or 2 heteroatoms selected from S, O and N,
(18) aryl, selected from phenyl and naphthyl, and
(19) heteroaryl, wherein heteroaryl is selected from the group consisting of:
  (a) imidazolyl,
  (b) isooxazolyl,
  (c) isothiazolyl,
  (d) oxadiazolyl,
  (e) oxazolyl,
  (f) pyridyl,
  (g) tetrazolyl,
  (h) thiazolyl,
  (i) thienyl and
  (j) triazolyl,
or when two members of the group R$_1$, R$_2$ and R$_3$ reside on the same carbon atom of Formula I, or two of the group R$_1$, R$_2$, R$_3$ and R$_4$ reside on adjacent atoms of Formula I, said two members along with the optional substituents thereon may optionally be joined, such that together with the carbon atom to which they are attached there is formed a saturated or unsaturated monocyclic ring of 5, 6 or 7 atoms, said monocyclic ring optionally containing up to three hetero atoms selected from N, O and S, R$_4$ is selected from the group consisting of:
  (a) hydrogen,
  (b) hydroxy,
  (c) amino,
  (d) cyano,
  (e) fluoro, chloro, bromo, and iodo,
  (f) trifluoromethyl,
  (g) C$_{1-6}$alkyl,
  (h) C$_{1-6}$alkoxy,
  (i) C$_{1-6}$alkylthio,
  (j) C$_{1-6}$alkylcarbonyl,
  (k) mono- and di-C$_{1-6}$alkylamino,
  (l) aryl, where aryl is phenyl and naphthyl,
  (m) aryloxy, where aryl is phenyl and naphthyl,
  (n) cycloalkyl, wherein the cycloalkyl is a 5-, 6-, or 7-membered monocyclic ring, and
  (o) heteroaryl, wherein heteroaryl is selected from the group consisting of:
    (1) pyridyl,
    (2) furanyl,
    (3) thienyl,
    (4) pyrazinyl,
    (5) pyrimidyl,
    (6) thiazolyl, and
    (7) triazolyl,
  each of (g) to (o) being optionally mono- or di-substituted, the substituents being independently selected from
    (1) hydroxy,
    (2) C$_{1-4}$alkyl,
    (3) C$_{1-3}$alkoxy,
    (4) amino,
    (5) mono- and di-C$_{1-6}$alkylamino,
    (6) carboxyl,
    (7) C$_{1-3}$alkylthio,
    (8) C$_{1-3}$alkyl-S(O)$_k$—, where k is 1 or 2,
    (9) C$_{1-4}$alkoxycarbonyl,
    (10) halo selected from fluoro, chloro, bromo, and iodo,
    (11) oxo, and
    (12) amidino, and R$_5$ is selected from the group consisting of:
  (a) hydrogen,
  (b) linear and branched C$_{1-12}$alkyl, optionally mono or di- substituted, the substituents being independently selected from:
    (1) hydroxy,
    (2) carboxy,
    (3) —NR$_7$R$_8$,
    (4) —OR$_7$,
    (5) —C(O)OR$_7$,
    (6) —S(O)$_k$R$_7$,
    (7) halo selected from F, Cl, Br and I,
    (8) trifluoromethyl and
    (9) phenyl, optionally mono or di-substituted with a substituent selected from hydroxy, halo, C$_{1-4}$alkyl, and C$_{1-4}$alkoxy,
  (c) —C(O)NR$_{10}$R$_{11}$, where R$_{10}$ and R$_{11}$ are each independently hydrogen, phenyl, cyclohexyl, —S(O)$_2$NR$_7$R$_8$ and optionally substituted C$_{1-6}$alkyl, wherein said substituent is selected from
    (1) —NR$_{12}$R$_{13}$, wherein R$_{12}$ and R$_{13}$ are each independently selected from H, C$_{1-6}$alkyl, phenyl and benzyl,
    (2) —OR$_{12}$,
    (3) —C(O)OR$_{12}$,
    (4) —S(O)$_k$R$_{12}$, where m is 0, 1 or 2,
    (5) halo selected from F, Cl, Br and I,
    (6) optionally substituted aryl wherein aryl and aryl substituents are as defined above,
    (7) optionally substituted heteroaryl wherein heteroaryl and heteroaryl substituents are as defined above,
    (8) optionally substituted C$_{5-10}$cycloalkyl wherein cycloalkyl and cycloalkyl substituents are as defined above, and
    (9) hetero C$_{5-10}$-cycloalkyl, wherein the hetero C$_{5-10}$cycloalkyl contains 1 or 2 heteroatoms selected from S, O and N,
  (d) —C(O)R$_{11}$,
  (e) —C(O)OR$_{11}$,
  (f) aryl, selected from phenyl and naphthyl, and
  (g) cyclohexyl.

12. The pharmaceutical composition according to claim 11 wherein:

R$_4$ is selected from the group consisting of:
  (a) hydrogen,
  (b) hydroxy,
  (c) amino,
  (d) cyano,
  (e) fluoro, chloro or bromo,
  (f) trifluoromethyl,
  (g) C$_{1-4}$alkyl,
  (h) C$_{1-4}$alkoxy,
  (i) C$_{1-4}$alkylthio, and
  (j) mono- and di-C$_{1-4}$alkylamino.

* * * * *